(12) United States Patent
Kremliovsky et al.

(10) Patent No.: US 7,729,753 B2
(45) Date of Patent: Jun. 1, 2010

(54) AUTOMATED ANALYSIS OF A CARDIAC SIGNAL BASED ON DYNAMICAL CHARACTERISTICS OF THE CARDIAC SIGNAL

(75) Inventors: Michael Kremliovsky, Poway, CA (US); Lev Korzinov, San Diego, CA (US)

(73) Assignee: CardioNet, Inc., San Diego, CA (US)

( * ) Notice: Subject to any disclaimer, the term of this patent is extended or adjusted under 35 U.S.C. 154(b) by 250 days.

(21) Appl. No.: 11/376,603

(22) Filed: Mar. 14, 2006

(65) Prior Publication Data

US 2007/0219453 A1    Sep. 20, 2007

(51) Int. Cl.
*A61B 5/046* (2006.01)

(52) U.S. Cl. .................... 600/518; 600/509
(58) Field of Classification Search .......... 600/508–521
See application file for complete search history.

(56) References Cited

U.S. PATENT DOCUMENTS

| | | |
|---|---|---|
| 4,646,754 A | 3/1987 | Seale |
| 5,047,930 A | 9/1991 | Martens et al. |
| 5,299,118 A | 3/1994 | Martens et al. |
| RE34,663 E | 7/1994 | Seale |
| 5,522,393 A | 6/1996 | Phillips et al. |
| 5,560,367 A | 10/1996 | Haardt et al. |
| 5,596,993 A | 1/1997 | Oriol et al. |
| 5,609,158 A | 3/1997 | Chan |
| 5,645,069 A | 7/1997 | Lee |
| 5,810,014 A | 9/1998 | Davis et al. |
| 5,827,195 A | 10/1998 | Lander |
| 5,921,937 A | 7/1999 | Davis et al. |
| 5,957,855 A | 9/1999 | Oriol et al. |
| 6,024,701 A | 2/2000 | Almog |
| 6,028,428 A | 2/2000 | Cunningham et al. |

(Continued)

FOREIGN PATENT DOCUMENTS

CN    2569743 Y    9/2003

(Continued)

OTHER PUBLICATIONS

"Hilbert Transform, Analytic Signal and the Complex Envelope", Signal Processing & Simulation Newsletter, http://www.complextoreal.com/tcomplex.htm. (2004).

(Continued)

*Primary Examiner*—Scott M Getzow
(74) *Attorney, Agent, or Firm*—Fish & Richardson P.C.

(57) ABSTRACT

Systems and techniques relating to locating cardiac wave forms in a cardiac signal, and to detecting a physiological condition, such as ventricular fibrillation. In general, in one aspect, a machine-implemented method includes obtaining a sensed cardiac signal of an organism, the sensed cardiac signal comprising a time series x(t); applying a Hilbert (H) transform to the time series x(t) to obtain H(x(t)), wherein x(t) and H(x(t)) together forming a partial state space trajectory; determining a speed of trajectory, for the sensed cardiac signal, from the partial state space trajectory; and identifying physiological information concerning the organism based on a combination of first and second signal elements, the first signal element including a phase property or an amplitude property of the speed of trajectory, and the second signal element including an amplitude property of the partial state space trajectory.

32 Claims, 10 Drawing Sheets

U.S. PATENT DOCUMENTS

| | | | |
|---|---|---|---|
| 6,069,975 | A | 5/2000 | Lehmann et al. |
| 6,076,015 | A | 6/2000 | Hartley et al. |
| 6,161,042 | A | 12/2000 | Hartley et al. |
| 6,216,031 | B1 | 4/2001 | Findeis et al. |
| 6,269,263 | B1 | 7/2001 | Ohnishi et al. |
| 6,278,961 | B1 | 8/2001 | Kadtke et al. |
| 6,340,346 | B1 | 1/2002 | Almog et al. |
| 6,368,283 | B1 | 4/2002 | Xu et al. |
| 6,370,437 | B1 | 4/2002 | Carter et al. |
| 6,377,843 | B1 | 4/2002 | Naydenov et al. |
| 6,381,559 | B1 | 4/2002 | Huang |
| 6,400,996 | B1 | 6/2002 | Hoffberg et al. |
| 6,401,057 | B1 | 6/2002 | Kadtke et al. |
| 6,442,421 | B1 | 8/2002 | Le Van Quyen et al. |
| 6,463,326 | B1 | 10/2002 | Hartley et al. |
| 6,507,749 | B1 | 1/2003 | Macgowan et al. |
| 6,507,754 | B2 | 1/2003 | Le Van Quyen et al. |
| 6,537,233 | B1 | 3/2003 | Rangayyan et al. |
| 6,561,986 | B2 | 5/2003 | Baura et al. |
| 6,564,176 | B2 | 5/2003 | Kadtke et al. |
| 6,569,101 | B2 | 5/2003 | Quistgaard et al. |
| 6,640,145 | B2 | 10/2003 | Hoffberg et al. |
| 6,651,025 | B1 | 11/2003 | Drepper |
| 6,728,691 | B1 | 4/2004 | Neuneier et al. |
| 6,731,990 | B1 | 5/2004 | Carter et al. |
| 6,732,064 | B1 | 5/2004 | Kadtke et al. |
| 6,735,466 | B1 | 5/2004 | Haghighi-Mood |
| 6,738,734 | B1 | 5/2004 | Huang |
| 6,950,702 | B2 | 9/2005 | Sweeney |
| 2001/0014776 | A1 | 8/2001 | Oriol et al. |
| 2002/0095099 | A1 | 7/2002 | Quyen et al. |
| 2003/0009399 | A1 | 1/2003 | Boerner |
| 2003/0065633 | A1 | 4/2003 | Nueneier et al. |
| 2003/0105499 | A1 | 6/2003 | Hartley et al. |
| 2003/0166995 | A1 | 9/2003 | Jansen |
| 2003/0233050 | A1 | 12/2003 | Haghighi-Mood et al. |
| 2004/0260169 | A1 | 12/2004 | Sternnickel |
| 2006/0084881 | A1 | 4/2006 | Korzinov et al. |
| 2007/0100213 | A1 | 5/2007 | Dossas et al. ............... 600/300 |

FOREIGN PATENT DOCUMENTS

| | | |
|---|---|---|
| WO | WO 03/071945 | 9/2003 |
| WO | WO 2006/044919 | 4/2006 |

OTHER PUBLICATIONS

"The QT Interval" 13-LEAD ECG's—A "Web Brain" for Easy Interpretation, http://medinfo.ufl.edu/~ekg/OT%20interval.html. (2006).

Benitez, D. et al. "The use of the Hilbert transform in ECG signal analysis", Computers in Biology and Medicine 31 (2001) 399-406.

Coast, D.A., et al., "An Approach to Cardiac Arrhythmia Analysis using Hidden Markov Models", Biomedical Engineering, IEEE Transactions on , vol. 37, Issue 9, Sep. 1990 pp., 826-836.

Daskalov, I. K., et al., "Automatic Detection of the Electrocardiogram T-Wave End", Medical & Biological Engineering & Computing, vol. 37, Issue 3, May 1999, pp. 348-353.

Daskalov, I. K., et al., "Electrocardiogram Signal Preprocessing for Automatic Detection of QRS Boundaries", Medical Engineering & Physics 21, 1999, pp. 37-44.

Goldberger, A. L. "Bhargava V: QRS Duration Measurement Using High-Frequency Electrocardiography: Applications and Limitations of a new Technique", Computers and Biomedical Research, vol. 15, Issue 5, Oct. 1982, pp. 475-484.

Gritzali, F. et al., "Detection of the P and T waves in an ECG", Computers and Biomedical Research, vol. 22, Issue 1, Feb. 1989, pp. 83-91.

Hamilton, P.S. et al., "Quantitative Investigation of QRS Detection Rules using the MIT-BIH Arrhythmia Database", IEEE Transactions on Biomedical Engineering 1986, BME-33, pp. 1157-1187.

Haykin, S., Editor, "Nonlinear Methods of Spectral Analysis", Topics in Applied Physics, vol. 34, Springer-Verlag, 1979.

Kay, S. M. et al., "Spectrum Analysis—A Modern Perspective", Proceedings of the IEEE, vol. 69, No. 11, Nov. 1981.

Kemmelings, J. G. et al., "Automatic QRS Onset and Offset Detection for Body Surface QRS Integral Mapping of Ventricular Tachycardia", Biomedical Engineering, IEEE Transactions on, vol. 41, Issue 9, Sep. 1994 pp. 830-836.

Laguna, P. et al., "Automatic Detection of Wave Boundaries in Multilead ECG Signals: Validation with the CSE Database", Computers and Biomedical Research, vol. 27, Issue 1, Feb. 1994, pp. 45-60.

Laguna, P. et al., "New Algorithm For QT Interval Analysis In 24-Hour Holter ECG: Performance And Applications", Med Biol Eng Comput. Jan. 28, 1990;(1), pp. 67-73.

Li, C. et al., "Detection of ECG Characteristic Points Using Wavelet Transforms", Biomedical Engineering, IEEE Transactions on vol. 42, Issue 1, Jan. 1995 pp. 21-28.

Meyer, C. R. et al., "Electrocardiogram baseline noise estimation and removal using cubic splines and state-space computation techniques", Computers and Biomedical Research, vol. 10, pp. 459-470, 1977.

Rao, B. D. et al., "Model based Processing of Signals: A State Space Approach", Proc. IEEE, vol. 80, pp. 283-309, Feb. 1992.

Sun, Yan et al., "Characteristic Wave Detection in ECG Signal Using Morphological Transform", BMC Cardiovascular Disorders (http://www.biomedcentral.com/content/pdf/1471-2261-5-28.pdf), Sep. 2005, pp. 1-7.

Thrane, N., Ph.D., "The Hilbert Transform", in Technical Review No. 3—1984.

Willems, J. L.., et al., "Influence Of Noise on Wave Boundary Recognition by ECG Measurement Programs, Recommendations for Preprocessing", Computers and Biomedical Research vol. 20, Issue 6 , Dec. 1987, pp. 543-562.

International Search Authority, International Search Report and Written Opinion for PCT/US2007/063916, Mailed Apr. 3, 2008, to be published by USPTO in this application (16 pages).

Bray et al., Use of Topological Charge to Determine Filament Location and Dynamics in a Numerical Model of Scroll Wave Activity, *IEEE Transactions on Biomedical Engineering* 49(10):1086-1093 (Oct. 2002), 8 pages.

Canadian Patent Office, Application No. 2,584,503, in Office Action dated Feb. 16, 2009, 6 pages.

Song-Kai et al., "The Real-Time Detection of QRS-Complex using the Envelop of ECG", IEEE Engineering in Medicine and Biology Society, 10th Annual International Conference, 1988, 1 page.

Australian Government IP Australia, in Australian Patent Application No. 2005295313, Examination Report dated Aug. 7, 2009, 2 pages (to be published by the USPTO).

Meyer, M. et al., "Stability of Heartbeat Interval Distributions in Chronic High Altitude Hypoxia," Oct.-Dec. 1998, *Intergrative Physiological and Behavioral Science,* 33(4):344-362, 19 pages.

Bhattacharya et al., "Universality in the brain while listening to music," Apr. 2001, Proceedings Royal Society London B., 268:2423-2433, 11 pages.

Electronic Records Administration, in Australian Patent Application Serial No. 2005295313, filed Oct. 18, 2005, Notice of Acceptance, mailed Dec. 10, 2009, 3 pages, to be published by the USPTO.

AUTOMATED ANALYSIS OF A CARDIAC SIGNAL BASED ON DYNAMICAL CHARACTERISTICS OF THE CARDIAC SIGNAL

CROSS REFERENCE TO RELATED APPLICATIONS

This application is related to U.S. application Ser. No. 11/081,401, filed Mar. 15, 2005 and entitled "MONITORING PHYSIOLOGICAL ACTIVITY USING PARTIAL STATE SPACE RECONSTRUCTION", which is hereby incorporated by reference.

BACKGROUND

The present application describes systems and techniques relating to automated analysis of a cardiac signal of an organism, for example, locating of onset, center and offset of P-wave, onset (Q) and offset (S) of QRS complex, and onset, center and offset of T-wave, and detecting a physiological condition from a cardiac signal obtained from a person.

The electrical activity of various organs, such as the heart or brain, can be monitored, and this electrical activity can be analyzed to look for patterns that may assist in diagnosing various conditions. For example, the electrical activity of the heart can be monitored to track various aspects of the functioning of the heart. Given the volume conductivity of the body, electrodes on the body surface or beneath the skin can display potential differences related to this activity. Anomalous electrical activity can be indicative of disease states or other physiological conditions ranging from benign to fatal.

Cardiac monitoring devices can sense the cardiac electrical activity of a living being and identify heart beats. Frequently, identification of heart beats is performed by identifying the R waves in the QRS complex, as can be seen in an electrocardiogram (ECG). The R wave represents ventricular depolarization. The typically large amplitude of this wave in the QRS complex is useful in identifying a heart beat. Traditional automated ECG signal analysis tools typically rely on correlation-based template matching and a number of empirical decision rules that are optimized for certain ECG databases. Many techniques have been developed for analyzing ECG signals, but further improvements are desirable.

SUMMARY

In general, in one aspect, a machine-implemented method includes obtaining a sensed cardiac signal of an organism, the sensed cardiac signal including a time series $x(t)$; applying a Hilbert (H) transform to the time series $x(t)$ to obtain $H(x(t))$, wherein $x(t)$ and $H(x(t))$ together forming a partial state space trajectory; determining a speed of trajectory, for the sensed cardiac signal, from the partial state space trajectory; and identifying physiological information concerning the organism based on a combination of first and second signal elements, the first signal element including a phase property or an amplitude property of the speed of trajectory, and the second signal element including an amplitude property of the partial state space trajectory.

The method can further include separating a phase component of the speed of trajectory into a slow component and a fast component, wherein the first signal element includes the phase property, the phase property being the slow component of the phase component. The determining can include estimating the speed of trajectory in discrete time in a digital processor using finite differences in the partial state space trajectory, and the identifying can include identifying the physiological information based on the phase property, the phase property being determined from the amplitude property of the speed of trajectory and a component of the speed of trajectory that corresponds to $H(x(t))$.

The identifying can include locating a P-wave center and boundaries based on the phase property and at least two thresholds. The identifying can include locating a T-wave end based on change in the combination relative to a determined T-wave center, the combination being the phase property of the speed of trajectory multiplied by the amplitude property of the partial state space trajectory. Moreover, identifying the physiological information can include locating a T-wave center in the sensed cardiac signal based on a momentum of trajectory derived from the amplitude property of the partial state space trajectory and the amplitude property of the speed of trajectory.

Identifying the physiological information can include estimating boundaries of a QRS complex in the sensed cardiac signal based on a momentum of trajectory derived from the amplitude property of the partial state space trajectory and the amplitude property of the speed of trajectory. Estimating the boundaries of the QRS complex can include locating a Q-point to the left of a maximum in the momentum of trajectory, and locating an S-point to the right of the maximum, based on a predefined portion of the maximum. In addition, the method can further include identifying an R-point based on the maximum in the momentum of trajectory.

Identifying the physiological information can include detecting ventricular fibrillation based on a momentum of trajectory derived from the amplitude property of the partial state space trajectory and the amplitude property of the speed of trajectory. Detecting ventricular fibrillation can include monitoring periodicity in oscillations of the momentum of trajectory. Detecting ventricular fibrillation can include maintaining a moving average of the momentum of trajectory; and monitoring changes in the momentum of trajectory relative to the moving average.

According to another aspect, a cardiac monitoring apparatus includes an input element; a processor; and a machine-readable medium encoding instructions operable to cause the processor to perform operations including obtaining, from the input element, a sensed cardiac signal of an organism; applying a Hilbert transform to the sensed cardiac signal to form a partial state space trajectory; determining a speed of trajectory, for the sensed cardiac signal, from the partial state space trajectory; combining an amplitude property of the partial state space trajectory with an amplitude property of the speed of trajectory to form a calculated signal; and identifying physiological information concerning the organism based on the calculated signal.

The combining can include forming a calculated signal including a momentum of trajectory. The identifying can include detecting ventricular fibrillation based on the momentum of trajectory. The identifying can include locating Q and S points in a QRS complex of the sensed cardiac signal based on the momentum of trajectory. The identifying can include locating a T-wave center in the sensed cardiac signal based on the momentum of trajectory.

The calculated signal can include a first calculated signal, the combining can include forming a second calculated signal from a phase property of the speed of trajectory and the amplitude property of the partial state space trajectory, and the identifying can include identifying the physiological information concerning the organism based on the first calculated signal and the second calculated signal. The identifying can include locating a T-wave end based on change in the second calculated signal relative to a T-wave center. The operations can include forming a third calculated signal from a phase property of the speed of trajectory; and the identifying can include identifying the physiological information concerning the organism based on the first calculated signal, the second calculated signal, and the third calculated signal.

The determining can include estimating a speed of trajectory, v(i), for the sensed cardiac signal, in discrete time t=i, i=[0 ... n], using finite differences in the partial state space trajectory, z(i). The first calculated signal can be calculated in accordance with |z(i)||v(i)|. The second calculated signal can be calculated in accordance with |z(i)|*Im(v(i))/|v(i)|. The third calculated signal can be calculated in accordance with Im(v(i))/|v(i)| or Re(v(i))/|v(i)|.

The identifying can include determining physiological quantities between identified boundaries and centers of wave modes including P-wave, QRS complex, and T-wave. The determining can include finding a first time difference between P-wave onset and Q-point (PR-interval), finding a second time difference between Q-point and S-point (QRS width), finding a third time difference between S-point and T-wave onset (ST segment), finding a fourth time difference between Q-point and T-wave offset (QT interval), finding a fifth time difference between S-point and a T-wave center (T-wave descend), finding a level of the sensed cardiac signal on the ST-segment, and finding a slope of the ST-segment in the sensed cardiac signal.

According to another aspect, a machine-readable medium encodes a computer program product operable to cause data processing apparatus to perform operations including obtaining a sensed cardiac signal of an organism, the sensed cardiac signal including a time series x(t); applying a Hilbert (H) transform to the time series x(t) to obtain H(x(t)), wherein x(t) and H(x(t)) together forming a partial state space trajectory; estimating a speed of trajectory, v(i), for the sensed cardiac signal, in discrete time t=i, i=[0 ... n], using finite differences in the partial state space trajectory, wherein the estimated speed of trajectory v(i) includes a first component corresponding to x(t) and a second component corresponding to H(x(t)); determining from v(i), by division, a phase property of the estimated speed of trajectory v(i) in accordance with a trigonometric function of phase; and identifying physiological information concerning the organism based on the phase property.

The identifying can include detecting wave form boundaries in the sensed cardiac signal. The detecting can include detecting the wave form boundaries based on the phase property combined with an amplitude property of the partial state space trajectory. The trigonometric function can be sine, and the determining can include dividing the second component of v(i) by an absolute value of v(i). The trigonometric function can be cosine, and the determining can include dividing the first component of v(i) by an absolute value of v(i).

The identifying can include locating a P-wave center and boundaries using the phase property, an identified Q-point, and at least two thresholds. The operations can include locating a T-wave center using a momentum of trajectory derived from an amplitude property of the partial state space trajectory and an amplitude property of the speed of trajectory, and the identifying can include locating a T-wave end based on change in a value relative to the T-wave center, the value being the phase property of the estimated speed of trajectory multiplied by the amplitude property of the partial state space trajectory. The obtaining can include receiving a real-time, electrocardiogram time series recorded previously for a human heart.

The described systems and techniques can be implemented in electronic circuitry, computer hardware, firmware, software, or in combinations of them, such as the structural means disclosed in this specification and structural equivalents thereof. This can include a program operable to cause one or more machines (e.g., a signal processing device including a programmable processor) to perform operations described. Thus, program implementations can be realized from a disclosed method, system, or apparatus, and apparatus implementations can be realized from a disclosed system, program, or method. Similarly, method implementations can be realized from a disclosed system, program, or apparatus, and system implementations can be realized from a disclosed method, program, or apparatus.

One or more of the following advantages may be provided. Improved automated identification of the location and boundaries of various wave forms in surface ECG analysis can be realized. In general, a heart beat cycle consists of P-wave (atrial depolarization), QRS complex (systole or ventricular depolarization), T-wave (repolarization of the ventricles) and U-wave (sometimes observed); altogether, the PQRSTU complex. The present systems and techniques can allow improved accuracy in the identification of these components of the heart beat cycle, and correspondingly, more accurate estimation of the time intervals in the PQRSTU complex that are of special interest to the medical and drug testing communities, such as PR interval (the time between the onset of the P-wave and the Q-point), QS interval (the duration of the QRS complex), ST segment (the part of the ECG between S-point and the onset of the T-wave), QT interval (the time between the onset of QRS complex, Q-point, and the end of T-wave), and T-wave descend (the time difference between S-point and a T-wave center). Such improved accuracy can also result in improved determination of additional information about the sensed cardiac signal based on the identified boundaries and centers of the wave forms, such as finding a level of the sensed cardiac signal on the ST-segment and finding a slope of the ST-segment in the sensed cardiac signal.

The present systems and techniques can enable increased accuracy in the detection of boundaries and transitions between different stages in the cardiac cycle in spite of the differences in their shapes and amplitudes observed in surface ECG recordings (variation in morphologies of ECG wave forms). These improvements may be realized even when input ECG signal amplitude is very small, and can thus result in a highly robust automated cardiac analysis system. Moreover, amplitude-phase properties of an ECG signal, which can be used in the automated analysis, can be readily and rapidly computed in a digital processor having limited resources. This can have significant benefits in real-time systems.

These and other features, aspects and advantages will be readily understood by those of ordinary skill in the art from a reading of the following detailed description in view of the accompanying drawings, which together set forth details of one or more embodiments. Moreover, it is to be appreciated that certain features of the present systems and techniques which are, for clarity, described below in the context of separate embodiments, may also be provided in combination in a single embodiment. Conversely, various features of the present systems and techniques which are, for brevity,

DRAWING DESCRIPTIONS

DETAILED DESCRIPTION

The systems and techniques described here enable partial reconstruction of heart dynamics from one- and two-lead systems, and allow a cardiac monitoring system to accurately locate P, Q, S and T points in, and to detect a physiological condition, such as ventricular fibrillation, from a cardiac signal obtained from a person. In general, the approach described here is based on the fact that an acquired electrical signal, such as an ECG signal, is a representation, or a projection, of the electrical activity of a biological system (e.g., the heart) onto some lead system. Reconstructing the dynamics of the heart from the available leads' signals can result in more accurate diagnosis of the heart's electrical activity. Partial reconstruction of the heart's dynamics can be performed using only a couple of leads. The systems and techniques described below (e.g., a Mobile Cardiac Outpatient Telemetry System) can result in improved diagnostics without requiring significant additional computational resources. Other advantages can include a more precise detection of fiducial points, used for such calculations as QRS width, ST segment and QT interval, a more accurate ventricular morphology analysis, and improved stability of the detection algorithm in the presence of noise.

FIGS. 1-8C and their corresponding description relate generally to U.S. application Ser. No. 11/081,401, filed Mar. 15, 2005 and entitled "MONITORING PHYSIOLOGICAL ACTIVITY USING PARTIAL STATE SPACE RECONSTRUCTION". Details of the present systems and techniques are described in connection with FIGS. 9-14. It is to be appreciated that the systems and techniques of the present application can be used in combination with those of U.S. application Ser. No. 11/081,401, and thus a full description of both is provided herein.

Figure 1:
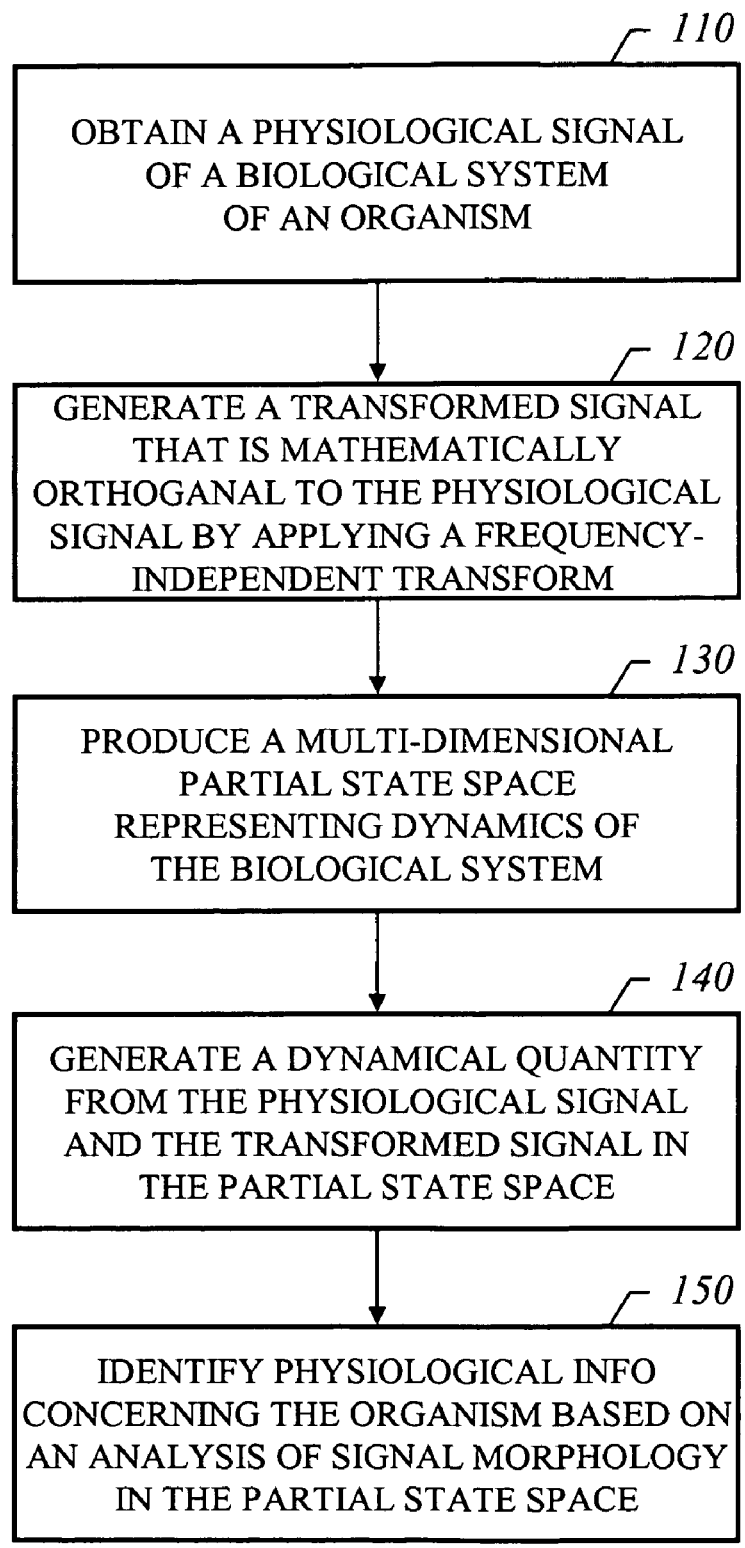
FIG. 1 is a flow chart illustrating monitoring of physiological activity using partial state space reconstruction.

FIG. 1 is a flow chart illustrating monitoring of physiological activity using partial state space reconstruction. A physiological signal of a biological system of an organism is obtained at 110. The physiological signal can be a cardiac signal, such as an ECG signal, a brain signal, such as an electroencephalogram (EEG) signal, a respiratory signal, a blood pressure signal, or other signals from an organism. The signal(s) can be obtained directly, such as by monitoring heart activity of a human patient as described further below, or the signal(s) can be obtained indirectly from another device or system. For example, the signal processing and analysis described herein can be performed in real-time as the signals are acquired and/or on stored signals retrieved from a database or other electronic storage devices.

A transformed signal is generated by applying a frequency-independent transform (e.g., a digital version of Hilbert transform) at 120. The transformed signal can be mathematically orthogonal (or effectively orthogonal) to the physiological signal, and the transform is frequency-independent in that it does not favor or amplify some frequencies of the signal over others. This frequency-independence can be particularly useful in analyzing biological signals, such as ECG data, where the frequency spectrum can easily cover a wide range of frequencies. For example, the heart's frequency spectrum can include frequencies as low as 1 Hertz and as high 100 Hertz.

Moreover, the frequency-independent transform can be a generally noise insensitive transform, such as Hilbert transform. This can be of tremendous value when analyzing signals sensed from biological systems, where the noise component of the signal may be significant. The Hilbert transform can be especially useful in this context, despite that fact that Hilbert transform imposes potential limits on what might otherwise be considered a preferred approach of full scale embedding for the biological system. A partial state space approach is nonetheless extremely useful given the typical dominance of a few major wave modes in the real-world sensed physiological signals.

A multi-dimensional partial state space is produced from the physiological signal and the transformed signal at 130. The partial state space is a partial reconstruction of a potential full state space for the biological system, and the full state space represents the dynamics of the biological system. Employing state space techniques, which are specific to the state space representation, to analyze biological system activity has been found to be quite effective, even when working only in a partial state space (i.e., a lower dimensional projection of a full state space).

Even a two dimensional partial state space (the original signal plus its Hilbert transform, with the third dimension of time being implicit) has been found highly effective in QRS detection as described below; and using a lower dimensional space can have significant advantages in terms of reducing the complexity of automated analysis (e.g., in some implementations, only a single lead and thus only a single input signal are needed). Using state space techniques on a partial state space to identify physiological information can be very effective in practice because the partial state space retains many properties of the original signal, while also adding properties specific to the state space representation. For example, noise in the original signal tends to have increasingly different/irregular dynamical behavior in higher dimensional space, and thus its detection and estimation can become an easier task in a physiological monitoring device or monitoring station in communication with such a device.

Obtaining the physiological signal can involve receiving an electrically-sensed time series x(t), generating a higher dimensional signal can involve applying Hilbert (H) transform to the time series x(t) to obtain H(x(t)), and producing the multi-dimensional partial state space can involve considering x(t) and H(x(t)) together as components of a state vector. These two variables, x(t) and H(x(t)), form a simple partial state space. Such procedure is also called embedding of x(t) into (partial) state space. For an implementation using multiple source signals (e.g., a multi-lead ECG input), x(t) is a multi-dimensional vector, in which case, both x(t) and H(x(t)) are vectors, and the partial state space has dimensions equal to twice that of x(t).

One or more dynamical quantities can be generated from the physiological signal and the transformed signal at 140. If a point in a state space describes particular dynamical state, dynamical quantities describe how this state evolves in space and time, for example, how physiological state evolves from point to point. For example, the generated dynamical quantities can be nonlinear transformations of x(t) and H(x(t)) in state space, excepting simple linear combinations of amplitude and phase. In general, a dynamical quantity can be used to characterize evolution of a dynamical state of the biological system.

Physiological information concerning the organism is identified, at 150, based on an analysis of signal morphology in the multi-dimensional partial state space. Identifying the physiological information can involve detecting a physiological occurrence for the biological system based on a dynamical quantity, which is a value derived from the combination of physiological and transformed signals as mentioned above. Additionally, identifying the physiological information can involve assessing multiple dynamical quantities with respect to one or more predefined physiological aspects of the biological system.

Figure 2:
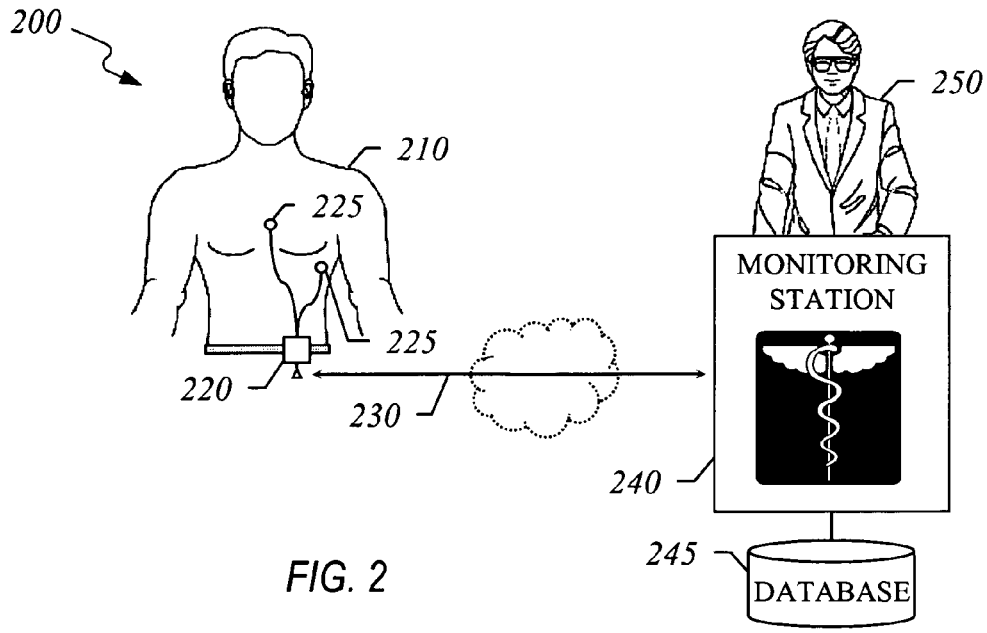
FIG. 2 illustrates a distributed cardiac activity monitoring system in which a cardiac signal is monitored for medical purposes.

FIG. 2 illustrates a distributed cardiac activity monitoring system 200 in which a cardiac signal is monitored for medical purposes. An organism 210 (e.g., a human patient, including potentially a healthy patient for whom cardiac monitoring is nonetheless deemed appropriate) has a cardiac monitoring apparatus 220 configured to obtain cardiac signals from the patient's heart. The cardiac monitoring apparatus 220 can be composed of one or more devices, such as a processing device and a sensing device. The sensing device can include two independent leads 225, which can receive electrical signals through body surface electrodes as shown (e.g., silver/silver chloride electrodes, which can be positioned at defined locations to aid in monitoring the electrical activity of the heart). As used herein, the term "lead" should be understood as including both a device that is subject to a potential difference that yields a voltage signal, such as an electrode that produces an ECG signal, and a conductor that forms a signal path to any signal amplifier used in the apparatus 220.

The cardiac monitoring apparatus 220 can communicate with a monitoring station 240 (e.g., a computer in a monitoring center) via a communications channel 230. The cardiac monitoring apparatus 220 can include one or more sensing, calibration, signal processing, control, data storage, and transmission elements suitable for generating and processing the cardiac signal, as well as for relaying all or a portion of the cardiac signal over the communications channel 230. The communications channel 230 can be part of a communications network and can include any suitable medium for data transmission, including wired and wireless media suitable for carrying optical and/or electrical signals. Wireless communications by the apparatus 220 can employ a suitable antenna as illustrated.

The cardiac monitoring apparatus 220 can communicate sensed cardiac signals, cardiac event information (e.g., real-time heart rate data), and additional physiological and/or other information to the monitoring station 240. The cardiac monitoring apparatus 220 can include an implantable medical device, such as an implantable cardiac defibrillator and an associated transceiver or pacemaker and an associated transceiver, or an external monitoring device that the patient wears or that is installed near the patient. Moreover, the cardiac monitoring apparatus 220 can be implemented using, for example, the CardioNet Mobile Cardiac Outpatient Telemetry (MCOT) device, which is commercially available and provided by CardioNet, Inc. of San Diego, Calif.

The monitoring station 240 can include a receiver element for receiving transmitted signals, as well as various data processing and storage elements for extracting and storing information carried by transmissions regarding the state of the individual 210. The monitoring station 240 can be located in the same general location (e.g., in the same room, building or health care facility) as the monitoring apparatus 220, or at a remote location. The monitoring station 240 can include a display and a processing system, and a system operator 250 (e.g., a doctor or a cardiovascular technician) can use the monitoring station 240 to evaluate physiological data received from the cardiac monitoring apparatus 220. The system operator 250 can use the monitoring station 240 to change operational settings of the cardiac monitoring apparatus 220 remotely during active cardiac monitoring of the person 210.

Moreover, the cardiac monitoring apparatus 220 and/or the monitoring station 240 can use the systems and techniques described herein to identify physiological information concerning the person 210. This can include signal processing and analysis on both an actively received signal and prior signals stored in a database 245. For example, historical signal information for a person can be used in conjunction with the systems and techniques described herein to improve analysis of currently acquired signals, and can facilitate heart beat classification and characterization of physiological conditions, which can assist a clinician or physician in making an appropriate diagnosis and prescribing an appropriate treatment.

Figure 3:
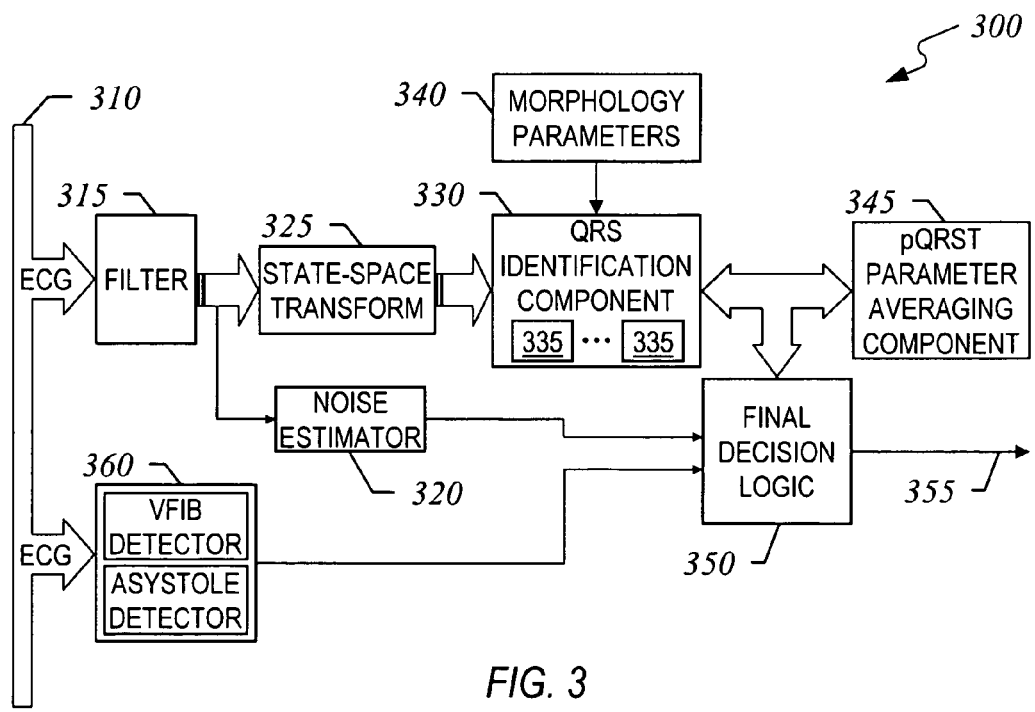
FIG. 3 is a block diagram illustrating an example QRS detector in a cardiac monitoring apparatus.

FIG. 3 is a block diagram illustrating an example QRS detector 300 in a cardiac monitoring apparatus. An ECG input element 310 includes a split output that provides an ECG signal to two processing paths within the QRS detector. A filter 315 operates on a first of these ECG signals to clean the signal as needed for later analytical processing. The filter 315 can be a filter bank, which can include a baseline shift remover, and one or more band pass filters configured to clean the ECG signal for various aspects of the later processing; the filter bank 315 can also split the ECG signal into separate signals for later parallel processing and/or include an analog-to-digital converter.

Output of the filter 315 can be provided to a noise estimator 320 and a state space transformation component 325. The state space transformation component 325 can generate a partial state space as described, such as by applying Hilbert transform directly to the ECG signal and providing both the ECG signal and the transformed ECG signal to a QRS identification component 330. It should be noted that applying the Hilbert transform "directly to" the ECG signal as shown (the intermediate filtering is not considered to negate this direct application of the Hilbert transform as such filtering does not constitute intermediate analytical processing) can have significant advantages in combination with the state space analysis techniques described; Hilbert transform can be applied at the front-end of the algorithm, rather than to some derivative of the cardiac signal. In addition, the state space transformation component 325 can effect noise cancellation in the process of transforming the signal, which can be a result of the partial state space the signal is transformed into. Note that, in general, a signal can be transformed arbitrarily before conversion to state space provided such preprocessing does not disturb the intrinsic dynamical relations persistent in the signal. Thus, a wide range of signal transformations can be applied prior to taking Hilbert without hurting the logic of state-space embedding.

The QRS identification component 330 is responsive to the output of the state space transformation component 325 and includes one or more dynamical quantity calculators 335, such as described further below. The QRS identification component 330 can perform signal analysis in the partial state space based on morphology parameters 340 provided to it, and the QRS identification component 330 can be coupled with both a pQRST parameter averaging component 345 and final QRS decision logic 350.

The final QRS decision logic 350 can base its QRS detector output 355 on input received from the QRS identification component 330, the pQRST parameter averaging component 345, and the noise estimator 320. This can include detecting heart beats, and can also include detecting a physiological occurrence by assessing one or more dynamical quantities with respect to one or more predefined physiological aspects of the human heart (e.g., classifying heart beats as normal or abnormal based on ventricular depolarization). In addition, the final decision logic 350 can also base its QRS detector output 355 on input received from an arrhythmia identification component 360 coupled with the split output of the ECG input 310. The arrhythmia identification component 360 can include a ventricular or atrial fibrillation detector and an asystole detector, which can employ various known techniques for identifying ventricular fibrillation and the absence of heart contractions.

The QRS detector 300 can be implemented in the monitoring station 240 and/or in the cardiac monitoring apparatus 220, the various components of which can be implemented as analog or digital components. The QRS detector 300 can be a real-time QRS detector that identifies successive QRS complexes and determines the beat-to-beat timing in real time (i.e., output data is generated directly from live input data). The beat-to-beat timing (RR-interval) can be determined by measuring times between successive R-waves. The QRS detector output 355 can be provided to additional logic, which can include logic to determine if an abnormal T wave potentially is occurring based on signal morphology analysis, an atrial fibrillation/atrial flutter (AF) detector, AF decision logic, and an event generator. Moreover, the sensed cardiac signal, or portions thereof, can be sent to a monitoring station, periodically, upon being interrogated and/or in response to identified events/conditions.

Figure 4:
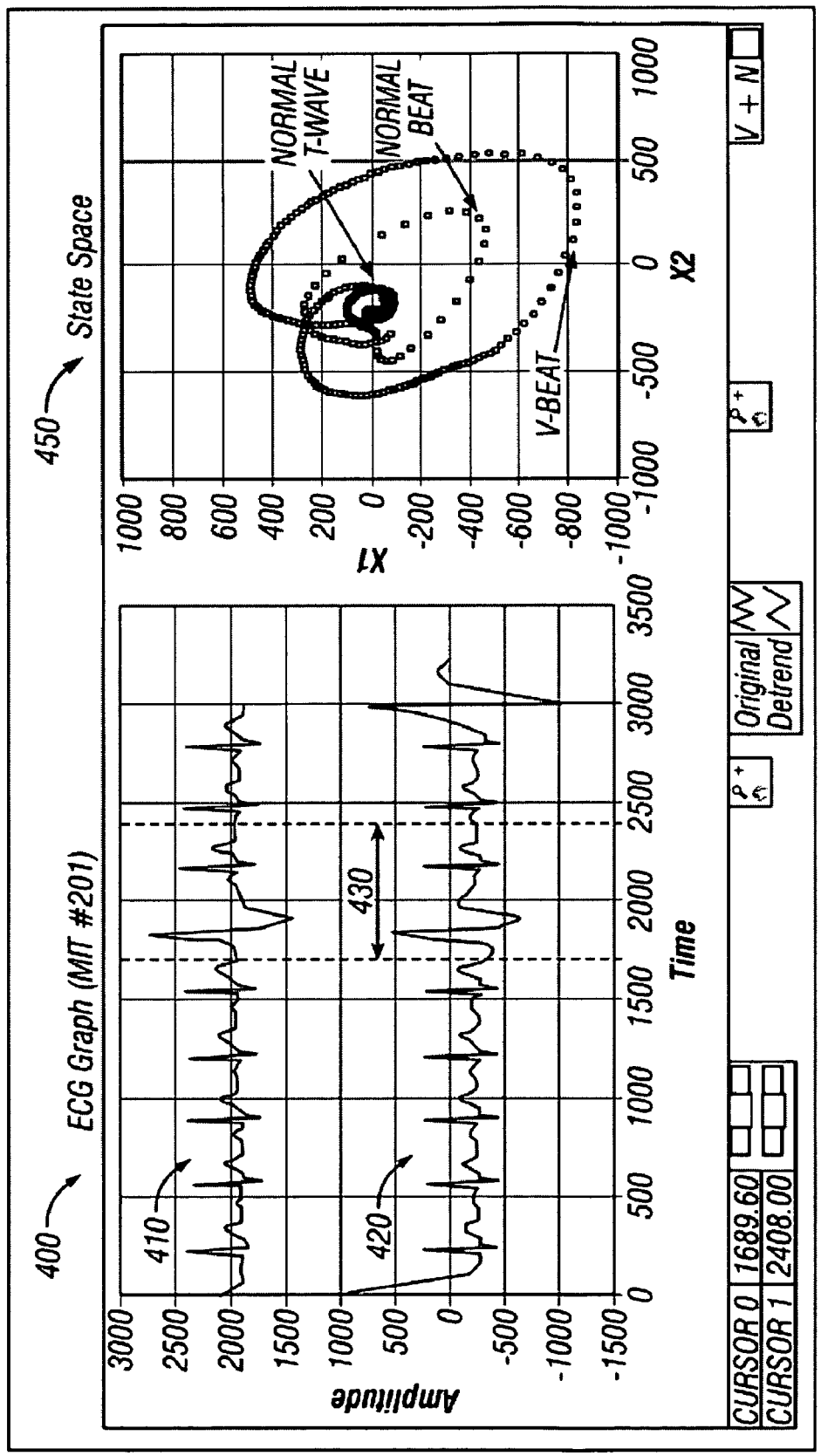
FIGS. 4, 8A, 8B and 8C illustrate a state space approach to beat morphology classification in partial state space reconstructed from surface ECG recording using Hilbert transform.

FIG. 4 illustrates a state space approach to beat classification based on distinction between normal and ventricular morphology. A first graph 400 shows an ECG signal 410 and its bandpass filtered version 420, with amplitude being the vertical axis and time being the horizontal axis. The heart cycle includes the traditionally recognized waveforms: the P wave, the QRS complex, the T wave, and the U wave. An abnormal heart beat is included in a time window 430, and a second graph 450 shows this abnormal heart beat presented in a partial state space.

The partial state space presents signal amplitude on the vertical axis and the Hilbert transform of the signal on the horizontal axis. Time is on the Z axis, which is perpendicular to the plane of the page. Thus, the time window 430 controls how many signal points are overlaid within the presented state space representation, and time is represented by the order in which the points are placed on the graph 450.

As can be seen, a normal beat is clearly differentiable from an abnormal Ventricular beat (e.g., by calculating how many points it takes to go through the big loops, which represent the QRS complex; the small loops shown are the T waves). Using this state space approach to cardiac signal analysis can be much more robust in practice than traditional analysis of a cardiac time series, because the state space approach is much less likely to be confused by a signal on any particular axis (note that the heart can be in different positions in the chest and/or relative to the lead). Although one or more graphs such as this can be employed in a user interface of a system, the main purpose of this graph is to illustrate the advantages of analyzing signal morphology in a multi-dimensional partial state space. In many applications, this analysis is expected to be fully automated, especially when the embedding space used has four or more spatial dimensions (plus the temporal dimension), which can be difficult for a human to visualize and understand.

Figure 5:
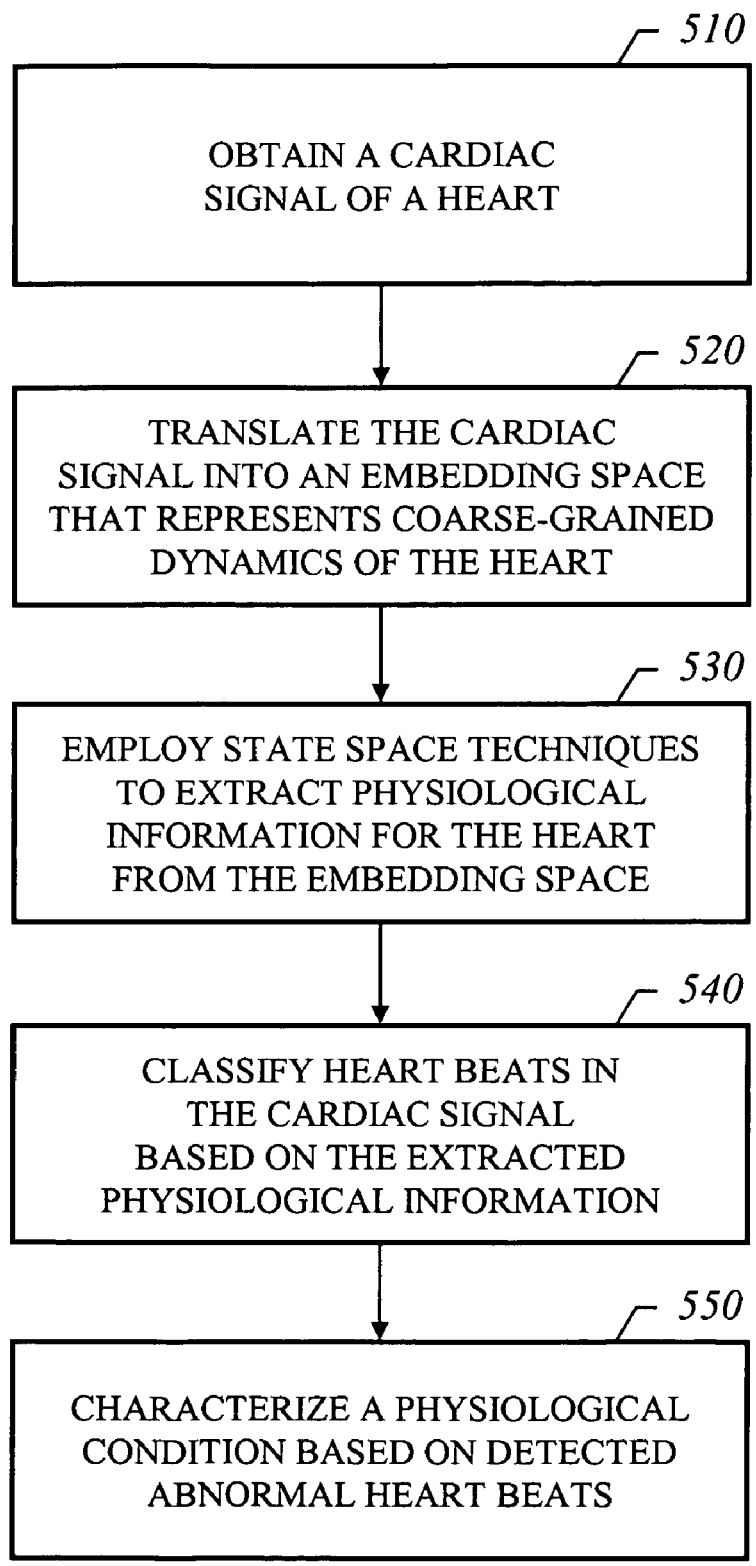
FIG. 5 is a flow chart illustrating a state space approach to classification of heart beats and characterization of a physiological condition.

FIG. 5 is a flow chart illustrating a state space approach to classification of heart beats and characterization of a physiological condition. A cardiac signal can be obtained at 510. The cardiac signal can be translated into an embedding space that represents coarse-grained dynamics of the heart at 520. For example, the embedding space can be made up from multiple cardiac signals from independent leads and the Hilbert transforms of the multiple cardiac signals.

State space techniques can be employed to extract physiological information for the heart from the embedding space at 530. This can involve deriving multiple dynamical quantities from the embedding space. This can include calculating three or more dynamical measures of heart activity and derivative physiological quantities, such as speed of trajectory, length of trajectory, area integral of a speed vector and threshold crossings in state space.

Speed of trajectory in state space can be defined as a dynamical quantity V(t), calculated as:

$$\vec{V}(t) = \frac{\vec{S}(t) - \vec{S}(t - \Delta t)}{\Delta t}, \quad (1)$$

where $\vec{S}(t)$ is a vector in the state space with coordinates x(t) and H(x(t)). Length of a trajectory in state space can be defined as a dynamical quantity L(t), which can be calculated as the sum of the point to point distances in state space; this is a nonlinear function of phase trajectory, which can be used to estimate system wandering (random deviation) from expected evolution. Area integral of a speed vector can be estimated as:

$$A(t) = \sum_{t=t_0}^{t_0 + n\Delta t} \left| \vec{V}(t) \otimes \left[ \vec{V}(t) - \vec{V}(t - \Delta t) \right] \right|, \quad (2)$$

where n∆t is the time interval where area A(t) is calculated. Threshold crossings in state space correspond to selected points in state space at which a trajectory crosses specific planes such as (x(t),0) or (0,H(t)). In general, intersection of phase trajectory and a selected surface is called Poincare mapping, and this mapping can be used to find onsets of state transitions, such as peaks of electrophysiological waves. Although three examples of dynamical quantities are described, it will be apparent that other state space analysis techniques can also be used, such as nearest neighbor techniques, calculation of topological defects, or variations of these.

The heart can be considered as a dynamical system, meaning that there are some deterministic (dynamical) laws governing the electrical pulses traveling through the heart tissue. Detailed reconstruction of heart dynamics is possible in theory, but often impractical because of the noise and variability in ECG data. However, for diagnostic purposes, full reconstruction is not necessary. Thus, partial reconstruction of the state space, representing coarse-grained dynamics of the heart, can be a highly effective approach to cardiac monitoring.

To illustrate this further, suppose a fully reconstructed multi-dimensional state space has been obtained. In this full state space, the reconstructed dynamics have a large amplitude when projected in some directions, and very small amplitude in other directions. By choosing a linear orthogonal transform that maximizes amplitude in two dimensions and minimizes the remaining projections, the first two dimensions represent large amplitude, coarse-grained dynamics, and other dimensions include lower amplitude, finer-grained dynamical movements. In addition, the finer-grained dimensions include noisy, less regular movements. Thus, the first two dimensions should be the most useful for diagnostic purposes because they predominantly represent dynamics of the biological system (the heart, in this example) and are less influenced by noise. Therefore, the first two dimensions can be used for diagnostic purposes. As should be appreciated in light of the above, instead of implementing a sequence of input signal→full state space→two dimensional coarse-grained state space, all that is needed is a direct transform of input signal→two dimensional coarse grained state space, which should provide substantially all the benefits of the first in a less computationally intensive procedure.

Heart beats in the sensed cardiac signal can be classified based on the extracted physiological information at 540. This can involve detecting abnormal heart beats as described above. A physiological condition can be characterized at 550. This can involve estimating a physiological condition based on detected abnormal heart beats. Such estimates or characterizations of a physiological condition can serve as a preliminary finding of a particular diagnosis for a patient.

Thus, in addition to detecting specific physiological events, such as heart beats, the present systems and techniques can be used to detect broader physiological occurrences, such as the development of a specific heart condition. This enables automated prediction of the probability of a given physiological condition and allows an automated system to propose a diagnosis for a patient. Such predictive capability can be very useful to a clinician or physician, and can be progressively improved upon as a database of physiological information is built over time.

In the context of heart monitoring, the present systems and techniques can be used to accurately identify the beginning and ending points of the heart waveforms, including P waves and U waves. This can enable more accurate calculation of physiological intervals, such as QT intervals, QS intervals, PR intervals and ST segment. Thus, an automated process employing these techniques can build a comprehensive record of heart waveform intervals for a patient, and use this record to facilitate later analysis and diagnosis of the patient's current condition. Relevant clinical information can be derived from lots of heart data, but only the most salient features of the data, as determined by an automated process, need be presented to the clinician or physician.

Figure 6:
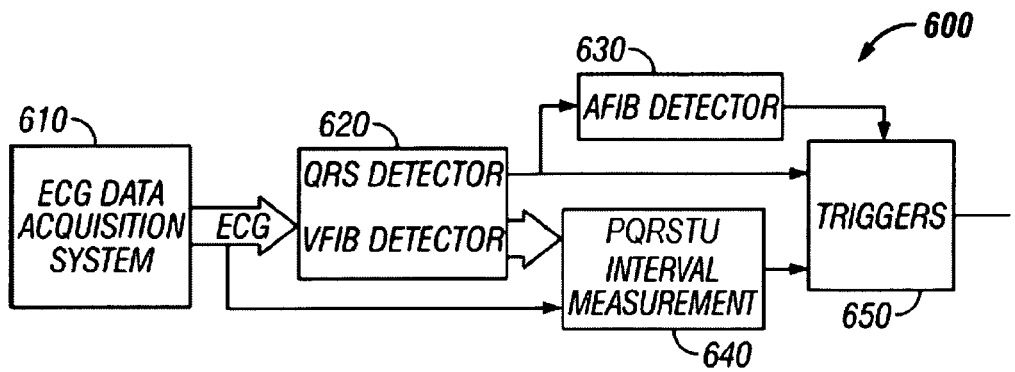
FIGS. 6 and 7 are block diagrams illustrating an example cardiac processing system and QRS detector.
Figure 7:
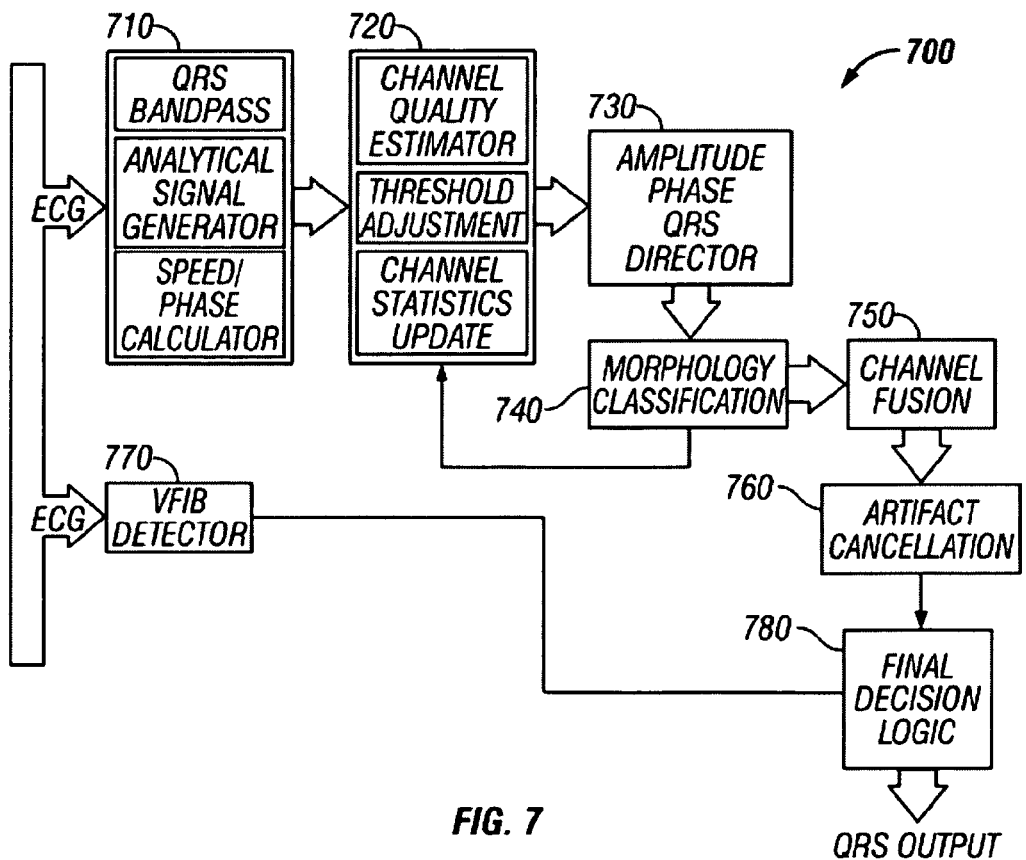

FIGS. 6 and 7 are block diagrams illustrating an example cardiac processing system 600 and QRS detector 700 employing the systems and techniques described above. The system 600 includes an ECG data acquisition system 610, which can employ fewer than ten leads. For example, the system 610 can be a two lead system as described above. The ECG data acquisition system 610 can provide a two-channel sampled ECG signal to a QRS and PQRSTU analysis package for processing (e.g., at a sample rate of 250 samples/second). Moreover, the input to the package can include the sampled data, pacemaker spike and invalid lead information (per sample), plus commands and configuration information.

A QRS and VFIB (ventricular fibrillation) detector 620 can analyze the input signal and provide output including QRS location and morphology information (e.g., normal, ventricular or unclassified) and a VFIB signal. An AFIB (atrial fibrillation) detector 630 can check for atrial fibrillation. A PQRSTU interval measurement component 640 can locate various portions of the cardiac signal (e.g., P-wave and T-wave) and can measure various intervals among located portions of the cardiac signal (e.g., PR interval, QS interval, ST segment, and QT interval), such as described further below. Moreover, the output of these components can be provided as input to one or more triggers 650 in an arrhythmia analysis system.

Figure 8A:
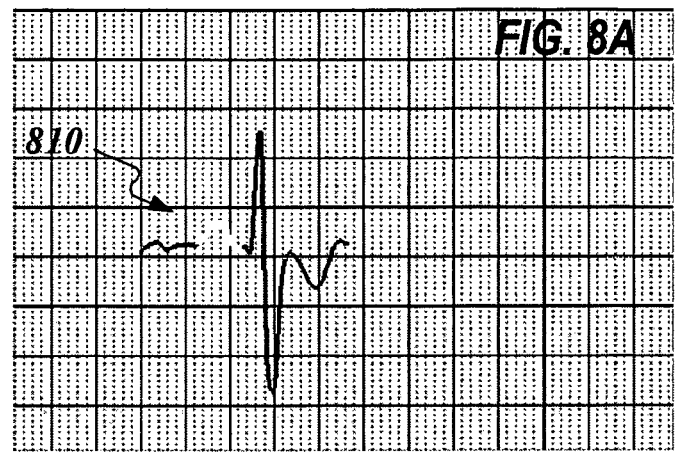
Figure 8B:
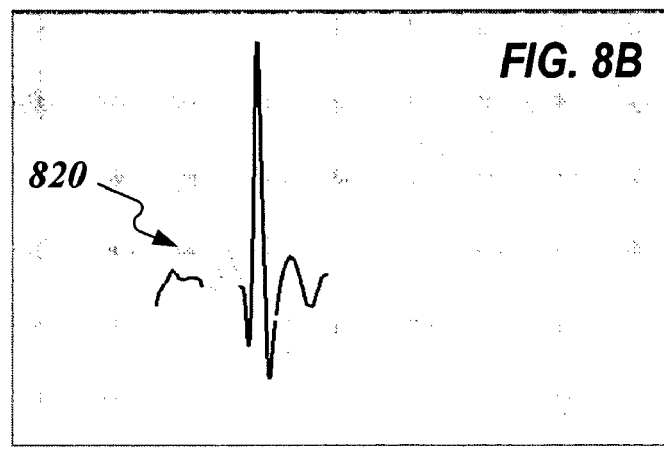
Figure 8C:
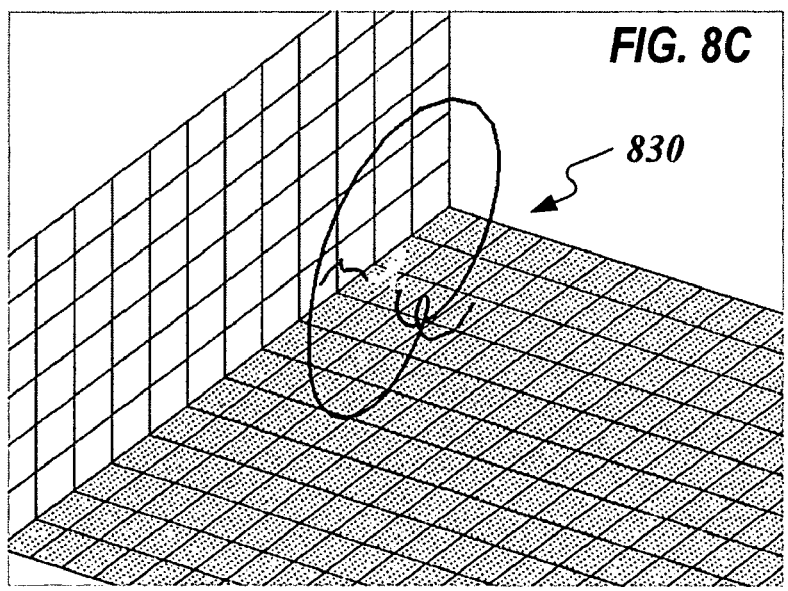

The QRS detector 700 includes a preprocessing stage 710, which can include a QRS bandpass component, an analytical signal generator and a speed/phase calculator. The preprocessing stage 710 can include a filter bank containing low and high pass filters and can construct the analytical signal as described above. For example, FIGS. 8A, 8B and 8C illustrate an original ECG signal 810, a Hilbert transform 820 of the ECG signal 810, and an analytical representation 830 of the ECG signal 810.

The preprocessing stage 710 can form a data stack used by the subsequent stages. The preprocessing stage 710 can convert incoming ECG data into a positively defined product characterizing the speed and the power of the heart's electrical activity (abbreviated below as speed-amplitude product). The preprocessing stage 710 can also provide filtered data to assist in low and high frequency noise estimation in later stages of the data analysis.

An update stage 720 can include a channel quality estimator, a threshold adjustment component, and a channel statistics update component. The channel quality estimator can report lead usability in the detection process. If one of the leads is off or not informative, the detection can be continued using the other lead. If both leads are classified by the channel quality estimator as not informative, a corresponding warning is generated.

Output of the update stage 720 can be provided to an amplitude-phase QRS detector 730. In general, QRS peak detection can involve calculation of a dynamic threshold, taking a previously detected peak as a starting point, and identification of the maximum above the threshold of the positively defined speed-amplitude product. Moreover, the detector can also be responsible for testing channel quality and adjusting itself to base line shifts and high amplitude high frequency noise. Channel quality can be estimated 250 samples (e.g., 1 second) ahead of the current sample.

A morphology classification stage 740 can employ RR' analysis (e.g., asymmetry, double notch detection), QS analysis (e.g., beat width), P-wave detection, T-wave detection, a ventricular morphology check, and additional wave form detection, such as described below in connection with FIGS. 9-14. After successful classification, a beat can be assigned certain metrics, which can be used to update beat statistics.

A channel fusion stage 750 can make a final decision on QRS correlation between the channels, quality of the beat (beat versus artifact) and ventricular morphology. At this stage, the channels can be merged into a single output. Moreover, programmable control can be provided over the output of additional information associated with the detected beat or channel quality. For example, the output can be set to include beat annotations (e.g., "N"=normal beat, "V"=ventricular beat, "Q"=not classified) and the time stamp corresponding to the detected center of the QRS complex. Extended annotations may include fiducial points (e.g., Q-points, S-points, P-wave location, and T-wave location) as well as channel characteristics (e.g., signal-to-noise ratio, detection confidence and so on).

Annotation of beats can start from the third beat detected and ventricular morphology can start from the fifth detected beat, if applicable. In general, the detector does not require learning, but in some implementations, two seconds delay may be needed for the preprocessing stage 710 to prepare filtered input and to adjust parameters. Moreover, a QRS complex can be classified as belonging to a group, and the groups can be used to update average QRS parameters to assist morphological analysis.

The QRS detector 700 can include an artifact cancellation component 760, and final decision logic 780 can generate QRS output based on input from the artifact cancellation component 760 and a VFIB detector 770. The QRS output can include a QRS-complex output for each detected QRS event. The QRS-complex output can include beat annotation and timing information. In addition, the QRS output can include QRS amplitude, QRS width and fiducial points information.

The VFIB detector 770 can detect ventricular fibrillation/flutter rhythms through analysis of the incoming ECG based on the following criteria: VFIB triggers when QRS-like activity is absent and the ventricular signal is above noise level (VFIB flag is true). If this event happens, then the QRS detector can be run in idle until the VFIB flag is set to false (VFIB is not detected). Alternatively, the VFIB detector 770 can use a partial state space trajectory as input and detect VFIB as described below.

The QRS detector 700 can also include asystole monitoring. The QRS detector 700 can use automatically adjusted thresholds. Lower limits in amplitude can be supplied as input parameters. Additionally, if a next QRS peak is not detected during ten seconds, the detector can give an asystole warning to assist external triggers.

Figure 9:
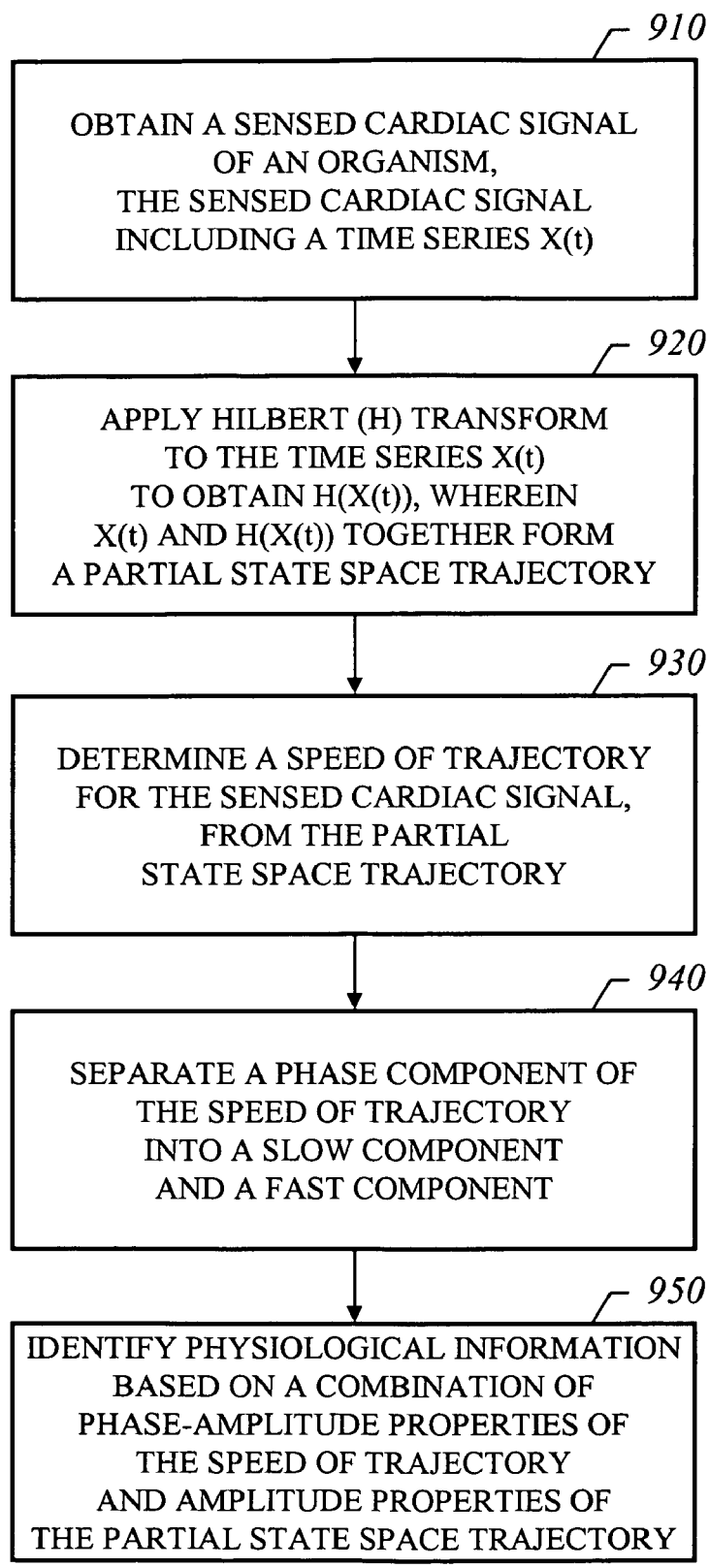
FIG. 9 is a flow chart illustrating a process of analyzing a cardiac signal based on dynamical characteristics of the cardiac signal.

FIG. 9 is a flow chart illustrating a process of analyzing a cardiac signal based on dynamical characteristics of the cardiac signal. The process of FIG. 9, and the detailed example implementations described below, can be implemented in cardiac monitoring apparatus and systems, such as those described above. A sensed cardiac signal of an organism is obtained at 910, where the sensed cardiac signal includes a time series $x(t)$. The time series $x(t)$ represents an input signal to an automated ECG analyzer. Hilbert (H) transform is applied to the time series $x(t)$ at 920 to obtain $H(x(t))$, wherein $x(t)$ and $H(x(t))$ together form a partial state space trajectory. Note that the input signal $x(t)$ can pass through a filter bank, such as described above, before the Hilbert transform. The resulting pair $[x(t), H(x(t))]$ represents an ECG signal in two dimensional $[x, y=H(x(t))]$ space, plus time t perpendicular to the $(x,y)$ plane. This can also be represented using a complex plane $z(t)=x(t)+iy(t)=r(t)\exp(i\phi(t))$, where $y(t)=H(x(t))$, $r(t)$ is the signal amplitude, and $\phi(t)$ is the signal phase.

A speed of trajectory, for the sensed cardiac signal, is determined at 930 from the partial state space trajectory. Note that the speed of trajectory here represents a vector in the state space (the speed of trajectory includes both a direction and an amount of speed). In digital representation, the time is discrete: $t=i$, $i=[0 \ldots n]$, and a speed of trajectory, $v(i)$, can be estimated using finite differences in the partial state space trajectory, $z(i)$: $v(i)=(z(i+k)-z(i-k))/(2k+1)$. Here, $v(i)$ is a complex number which can also be represented in amplitude-phase form: $v(i)=|v(i)|\exp(i\theta(i))$, where $\theta(i)$ is the phase of the speed of trajectory $v(i)$, and $|v(i)|$ is the absolute value of the speed of trajectory. Note that complex functions (having both real and imaginary components) are used here for the purpose of clarity in this description, and should not be ascribed some special meaning. The systems and techniques described here can be implemented using real numbers and scalar projections of vectors.

The description below focuses on implementations that estimate the speed of trajectory in discrete time in a digital processor using finite differences in the partial state space trajectory. However, other techniques can also be used to determine the speed of trajectory. For example, in the case of noisy input signals, the least squares fit technique can be used to estimate the derivative of the partial state space trajectory. Nonetheless, since many implementations will employ smoothing procedures (such as filtering) to preprocess ECG data to remove any high frequency noise component, the finite differences approach to estimating the partial-state space trajectory is sufficient, and can even have significant advantages when used with the low resource processors that are typical in portable ECG monitoring apparatus.

In addition, in the presence of noise, the phase $\theta(i)$ can be separated at 940 into slow and fast components: $\theta(i)=\theta_s(i)+\theta_f(i)$. The fast component, $\theta_f(i)$, reflects the influence of noise, but can be effectively neutralized by smoothing. The slow changing component, $\theta_s(i)$, still reflects the relevant dynamic behavior of the heart, as discussed further below.

Physiological information concerning the organism is identified at 950 based on a combination of phase-amplitude properties of the speed of trajectory and amplitude properties of the partial state space trajectory. The combinations can include a combination of an amplitude property of the partial state space trajectory and an amplitude property of the speed of trajectory. For example, a momentum of trajectory, $M(i)$, can be derived from an amplitude property of the partial state space trajectory and an amplitude property of the speed of trajectory: $M(i)=|z(i)||v(i)|$. This is referred to as a momentum function because of its similarity with a common definition of angular momentum in physics.

The combinations can also include a combination of an amplitude property of the partial state space trajectory and a phase property of the speed of trajectory. For example, the phase property of the speed of trajectory can be used to locate a P-wave to the left of a QRS complex identified using the momentum of trajectory, $M(i)$. In addition, the phase property of the speed of trajectory can be directly combined with an amplitude property of the partial state space trajectory, such as to detect the end of a T-wave.

To better understand the various available combinations, consider the following. The imaginary line of minimal ECG activity, as seen in a surface ECG signal, is called the "isoelectric" line. On the isoelectric line, the real (Re) component of the speed of trajectory goes to zero: $Re(v(i)) \rightarrow 0$ on the isoelectric line of an ECG signal. This corresponds to simultaneous $\theta(i) \rightarrow \pm \pi/2$, and $|v(i)| \rightarrow 0$. When a wave form change takes place (increase or decrease), Re(v(i)) is large, reflecting a quick change in signal amplitude.

The phase $\theta(i)$ of the speed of trajectory does not generally depend on the absolute position of the isoelectric line. Nonetheless, the wave forms in the ECG signal are reflected in accumulation of phase (directed change) between points on isoelectric lines, where $\theta_s(i)$ takes limiting and slowly changing values while $\theta_f(i)$ oscillates disorderly. The behavior of $\theta(i)$ is generally persistent even when the signal amplitude is very small. This can have significant implications for the robustness of the analysis techniques described herein. Moreover, in the presence of noise, the slow changing component $\theta_s(i)$ (discussed above) still reflects this behavior.

Although $\theta(i)$ can be used directly, it need not be. Rather, $\theta(i)$ can be used indirectly by using a phase property that depends on $\theta(i)$ and that is simpler to calculate. A phase property of the speed of trajectory v(i) can be determined from v(i) in accordance with a trigonometric function, using the real component of v(i), the imaginary (Im) component of v(i), or both. For example, the ECG analysis apparatus can use $\sin(\theta(i))=\text{Im}(v(i))/|v(i)|$ and $\cos(\theta(i))=\text{Re}(v(i))/|v(i)|$. These phase properties can be readily and rapidly computed in a digital processor having limited resources. This can have significant benefits in real-time systems. Moreover, these trigonometric functions have convenient properties in that they vary in a strictly limited interval [−1,1], and together they uniquely identify the phase $\theta(i)$ with up to $2\pi n$ difference.

The identification of physiological information at 950 can include locating the center and boundaries of the different wave forms in one or more surface ECG signals. Moreover, this identification of physiological information can include precise identification of various intervals between wave forms, which are of special interest to the medical and drug testing communities. Such intervals can include PR interval (the time between beginning of P-wave and Q-point), QS interval (the duration of QRS complex), ST segment (the part of the ECG between S-point and the beginning of T-wave), QT interval (the time between the onset of QRS complex, Q-point, and the end of T-wave), and T-wave descend (the time difference between S-point and a T-wave center). Additional information about the sensed cardiac signal can also be determined based on the identified boundaries and centers of the wave forms, such as finding a level of the sensed cardiac signal on the ST-segment and finding a slope of the ST-segment in the sensed cardiac signal.

Detailed examples of the identification of physiological information are described below in the context of a single (scalar recording) ECG signal. However, it should be understood that all of these techniques can be implemented using more than one channel/lead representing the ECG signal, and the state space transformation can be performed on all components. Thus, a combined analysis of multiple inputs from multiple leads can also be implemented.

Figure 10:
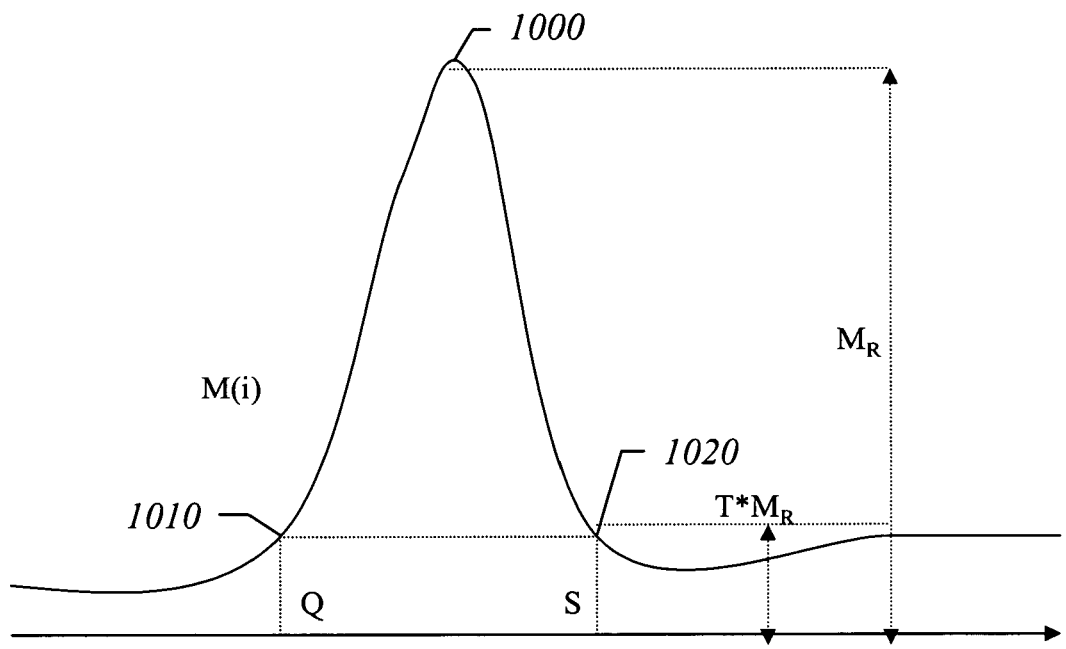
FIG. 10 shows an example approach to estimating the boundaries of the QRS complex in a cardiac signal.

FIG. 10 shows an example approach to estimating the boundaries of the QRS complex in a cardiac signal. The center of a heart beat (R-point 1000) can be located using the QRS detector described above, or by other techniques. Given the R-point 1000, the momentum of trajectory, $M(i)=|z(i)||v(i)|$ can be used to estimate the boundaries of the QRS complex. M(i) is non-negatively defined (takes only non-negative values). M(i) has a maximum in close proximity to the R-point 1000 and descends on both sides of the maximum. Letting $M(i)=M_R$ be the value of the M function at its maximum, Q-point 1010 can be located to the left of R, and S-point 1020 can be located to the right of R, based on a predefined portion of the maximum. Different predefined portions of the maximum can be used in identifying Q-point 1010 and S-point 1020, or a single predefined portion can be used in identifying both Q-point 1010 and S-point 1020. For example, both Q-point 1010 and S-point 1020 can be identified as the points where M(i) descends to the level of $T*M_R$, where T=0.2. Empirically, the parameter T is generally found to be in the range [0.1, 0.5] depending on spectral characteristics of any smoothing filters used in connection with calculation of the momentum of trajectory.

Figure 11:
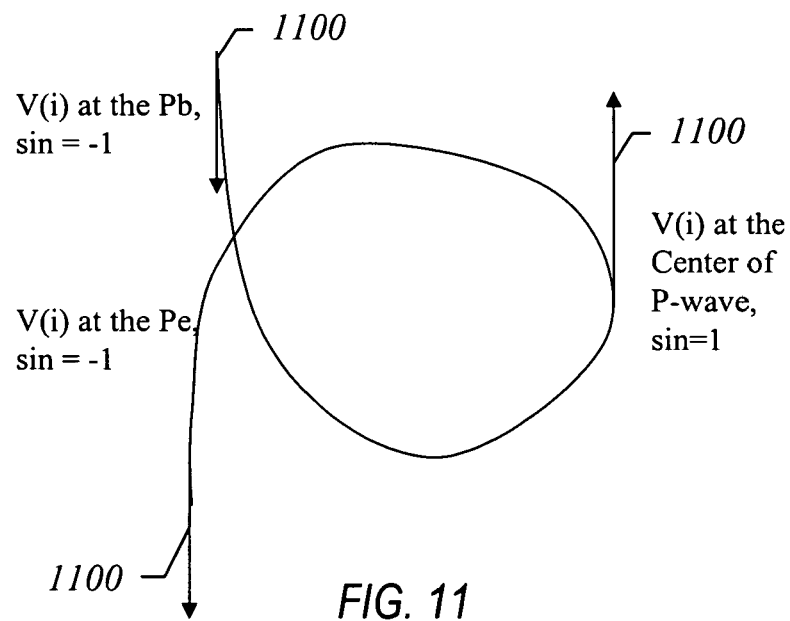
FIG. 11 shows an example of a speed of trajectory's change in direction and phase over time during detection of a P-wave in state space.

FIG. 11 shows an example of a speed of trajectory's change in direction and phase over time during detection of a P-wave in state space. In this example implementation of P-wave detection, positive or bipolar P-waves are detected. However, as will be readily understood, the general techniques being described can be readily modified to handle, and are equally applicable to all kinds of P-wave morphologies. In general, the center and boundaries of a P-wave can be located based on a phase property of the speed of trajectory and at least two thresholds.

In the present example, the center of a P-wave can be located as the closest maximum of $\sin(\theta(i))=\text{Im}(v(i))/|v(i)|$ to the left of Q-point, which maximum is also above a certain threshold $T_P$. The threshold $T_P$ is an empirically derived number, typically close to 1 (e.g., $T_P=0.9$). Consequently, the sine of the phase $\theta(i)$ descends to the left and to the right from the center of the P-wave. P-wave boundaries ($P_b$ and $P_e$) can be located as the points at which $\sin(\theta(i))$ reaches a negative threshold value $T_{Pb}$, (e.g., $T_{Pb}=-0.9$) or minimum, whichever is reached first. The physical meaning of this approach is determined by the shape of P-wave in the state space representation of ECG. As shown in FIG. 11, the speed of trajectory 1100 performs a full phase rotation through the course of the P-wave.

In practice, the degree of phase accumulation and the position of the speed of trajectory at the apex of a P-wave may vary depending on P-wave morphology and possible collision with the neighboring wave forms (like T-wave from the preceding heart beat). However, in a typical embodiment, the parameters $T_P$ and $T_{Pb}$ can be selected universally to accommodate for the majority of morphologies and ranges of heart rates.

Figure 12:
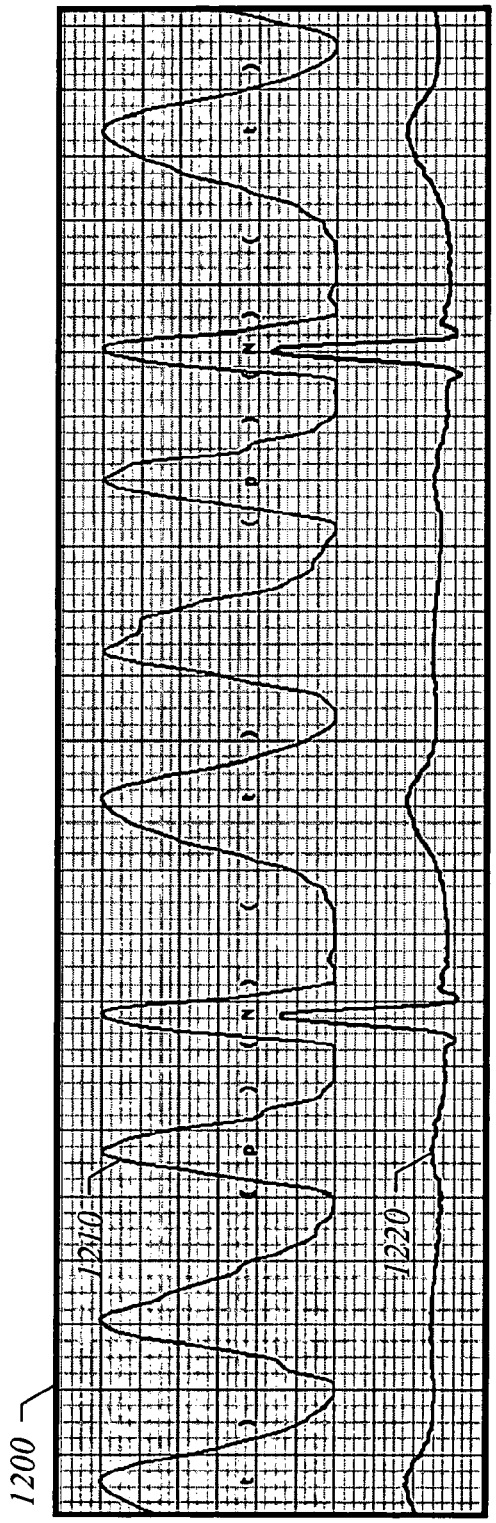
FIG. 12 is a chart showing an example phase property of a speed of trajectory plotted along with an ECG signal.

The general behavior of $\sin(\theta(i))$ is represented in FIG. 12, which shows a chart 1200 of the phase property $\sin(\theta(i))$ 1210 plotted along with an ECG signal 1220. The phase property $\sin(\theta(i))$ 1210 shows the locations of P-wave, QRS, T-wave and U-wave on the actual ECG 1220. As shown, the detector can annotate the parts of PQRST complex (e.g., P-wave annotated by "(P)", QRS annotated by "(N)", and T-wave annotated by "(t)") based on observed behavior of the phase (opening bracket "(" indicates the beginning/onset of a wave form while closing bracket ")" indicates its end/offset). In the example of FIG. 12, the phase has not been smoothed; the ECG 1220 here is record 103 from the MIT-BIH (Massachusetts Institute of Technology/Beth Israel Hospital) ECG database.

As shown, the phase can be readily used to locate various parts of the PQRST complex. Moreover, while both P-waves and U-waves are small in amplitude, their phase accumulation clearly shows the boundaries of these wave forms. In general, trigonometric functions of phase of the trajectory's speed in state space, such as $\sin(\theta(i))=\text{Im}(v(i))/|v(i)|$ or $\cos(\theta(i))=\text{Re}(v(i))/|v(i)|$, can be used to detect wave form boundaries in PQRSTU complex, especially in the cases where the amplitude of the wave form is small.

Accurate detection of the P-wave beginning point in combination with the detection of Q-point (such as described above in connection with FIG. 10) provides data for calculating the PR interval (the distance between the beginning of P-wave and Q-point, the onset of QRS). This interval can be used as an important measure to characterize anomalies in heart rhythms as well as a measure of drug influence on the cardiovascular system.

In addition to using the phase of the speed of trajectory, as described above, the phase can also be used in functional combinations with other parameters, such as the amplitude of the partial state space trajectory, $A(i)=|z(i)|$. Since phase is not defined when $A=0$, the discontinuities in the phase can be suppressed, for example, by the product $A_s(i)=A(i)*\sin(\theta(i))=|z(i)|*Im(v(i))/|v(i)|$. This represents a combination of a phase property of the speed of trajectory, $v(i)$, and an amplitude property of the partial state space trajectory, $z(i)$. Moreover, this combination generally has extremes that point to wave form boundaries in the PQRST complex. Thus, this combination (and variations of it) can be very valuable in automated cardiac analysis since it readily identifies waveform boundaries by having its extremes at the points of waveform change.

Figure 13:
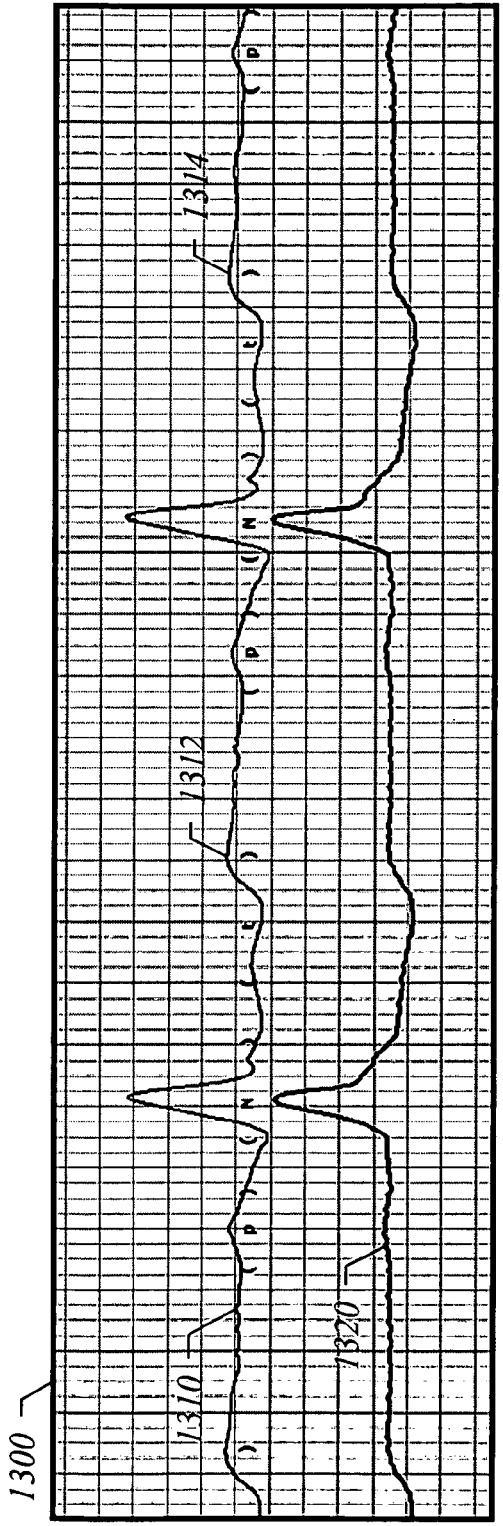
FIG. 13 is a chart showing an example combination (e.g. product) of a phase property of a speed of trajectory and an amplitude property of a partial state space trajectory, plotted along with an ECG signal.
Figure 14:
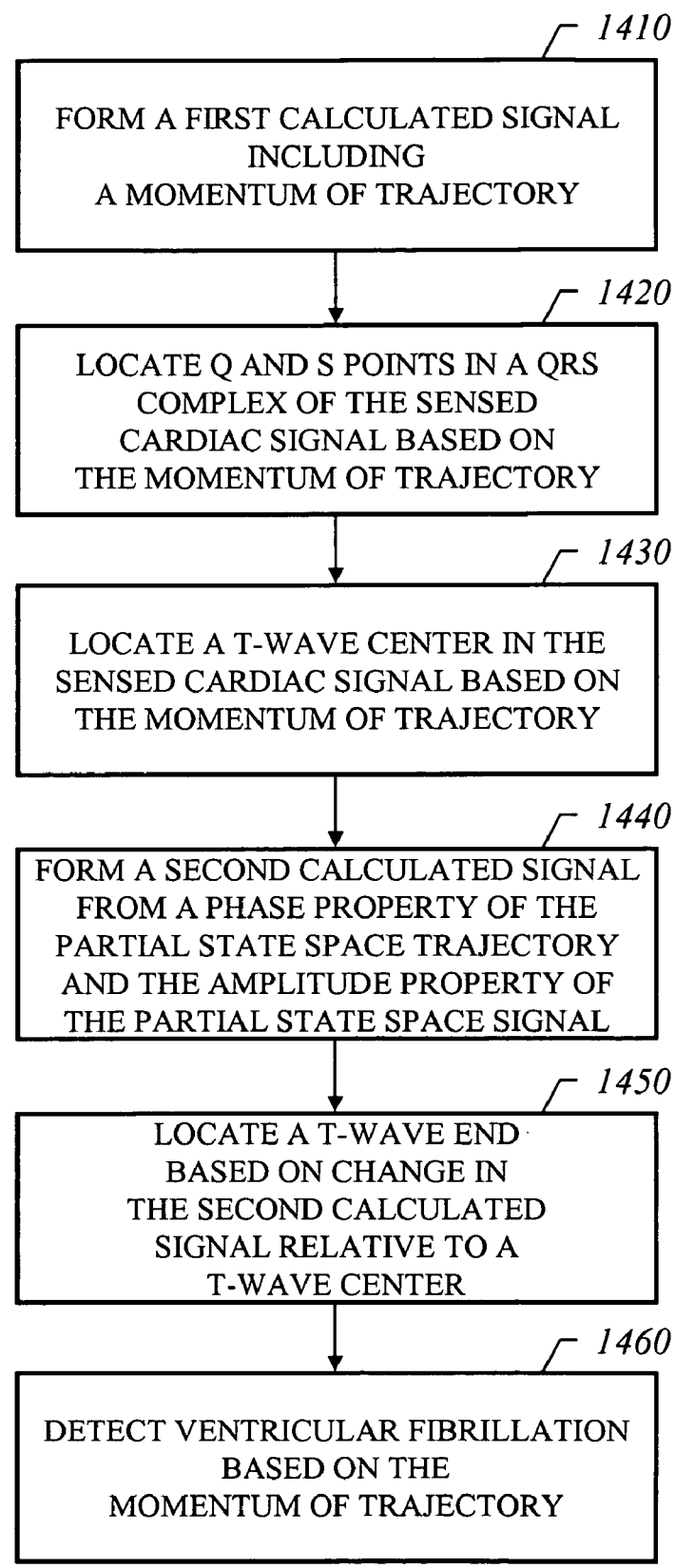
FIG. 14 is a flow chart illustrating example techniques for identifying physiological information concerning an organism based on dynamical characteristics of a cardiac signal.

FIG. 13 is a chart 1300 showing an example combination 1310 of a phase property of a speed of trajectory and an amplitude property of a partial state space trajectory, plotted along with an ECG signal 1320. The ECG 1320 here is record 214 from the MIT-BIH ECG database. While there is no well defined end of T-wave as seen from ECG 1320, the product 1310 shows these points as extremum 1312 and 1314. Thus, the transformation of the input ECG, and the use of the phase of the speed of trajectory in combination with the amplitude of the partial state space trajectory makes it much easier for an algorithm to detect fiducials in the ECG input. As shown in FIG. 13, there can also be a distinct performance on P-wave detection.

In addition to the techniques described above, FIG. 14 is a flow chart illustrating additional techniques for identifying physiological information concerning an organism based on dynamical characteristics of a cardiac signal. A first calculated signal including a momentum of trajectory can be formed at 1410. This can be the momentum of trajectory $M(i)$ described above in connection with FIG. 10, and as discussed above, Q and S points can be located in a QRS complex of the sensed cardiac signal at 1420 based on the momentum of trajectory (or close approximations of it).

A T-wave center can be located at 1430 in the sensed cardiac signal based on the momentum of trajectory. This can involve using finding the maximum of the momentum function $M(i)$ following the located S-point.

A second calculated signal can be formed at 1440 from a phase property of the speed of trajectory and the amplitude property of the partial state space trajectory. This can involve calculating the second calculated signal in accordance with the amplitude-phase function $A_s(i)=A(i)*\sin(\theta(i))=|z(i)|*Im(v(i))/|v(i)|$. In general, this amplitude-phase function (or its close approximations) can be used to detect wave form boundaries with high precision when both amplitude and phase of the trajectory's speed are important for the detection to be accurate.

For example, T-wave detection is typically more complicated than P-wave detection due to the larger variety of possible morphologies. A T-wave end can be located at 1450 based on change in the second calculated signal relative to a T-wave center. The T-wave center can be found using the maximum of the momentum function $M(i)$ following S-point, or by other techniques. Given the T-wave center ($T_c$), a T-wave end detector can search for the extremes of the amplitude-phase function $A_s(i)=A(i)*\sin(\theta(i))=|z(i)|*Im(v(i))/|v(i)|$ to the right of $T_c$. If $A_s(i)$ is at maximum around $T_c$, then the end of T-wave ($T_e$) corresponds to the following minimum of $A_s$. If $A_s(i)$ is at minimum around $T_c$, then the end of T-wave ($T_e$) corresponds to the following maximum of $A_s$ (e.g., 1312 and 1314 in FIG. 13). This method can give a very consistent determination of T-wave end based on a combination of amplitude and phase properties.

This method may be further improved by including additional factors in the T-wave end detection, such as phase of speed turning points (in analogy to the P-wave detection method described above). For example, the phase of the trajectory speed shows similar behavior as in the case of P-wave detection. The boundaries of T-wave can be determined as points at which phase crosses predefined thresholds ($T_{tb}$) in a similar way as described above in connection with FIG. 11. This correction to the T-wave detection can aid in difficult cases when the beginning of T-wave is not found using the $A_s(i)$ function. The modified method looks for either an extremum of the $A_s(i)$ function or an extremum of phase whichever is found first. The accurate detection of T-wave end point in combination with the detection of Q-point described above provides data for calculating QT interval. This interval can be used as an important measure to characterize the effects of drugs on the cardiovascular system in clinical trials.

In addition, ventricular fibrillation can be detected at 1460 based on the momentum of trajectory. Ventricular fibrillation (VFIB) is a near fatal heart condition characterized by sporadic ventricular contraction and very low cardiac output. Detecting VFIB promptly is important and involves recognizing that the regular PQRST complex is not present in the ECG signal. VFIB detection can be accomplished using the momentum of trajectory, based on the observation that the momentum function $M(i)$ tends to oscillate with high periodicity and tends to avoid levels close to zero during VFIB episodes. Contrary to VFIB, in normal rhythms, the M function shows prolonged intervals of small variations corresponding to the low speed movements in the vicinity of the isoelectric line, interrupted by bursts corresponding to QRS complexes.

To detect the transition between a QRS-based rhythm and VFIB, the following method can be used. A moving average <M> of the M function can be calculated in a window of a certain duration, for example 1 second. Then statistics regarding how often $M(i)$ is above <M> ($N_{above}$) relative to the time spent below <M> ($N_{below}$) can be accumulated for a middle point in the window on a run-time basis. The ratio of $N_{above}/N_{below}$ can then be used to signal transition to VFIB. For example, if $N_{above}/N_{below}$ is greater than a certain critical level found empirically (e.g., 0.4), this indicates VFIB episode onset. A different level (e.g., 0.2) can be used then to indicate the VFIB episode offset. The lower value for the VFIB offset is used to prevent premature exit from VFIB episode since this heart condition is very dangerous and calls for additional safety. To improve detection accuracy in the presence of high noise an additional inertia can be added to the detector.

For example, for VFIB flag to be raised VFIB onset can be detected during all 125 consecutive data points (0.5 seconds of data). Detection of VFIB offset can also be supplied with inertia, for example, VFIB flag can be dropped if VFIB offset is detected during 250 consecutive data points (1 second of data). The severity of VFIB episode depends, in part, on its duration. It is generally believed that surviving more than 10 minutes in VFIB condition is unlikely. The VFIB detector can take into account the overall duration of a VFIB episode. Additional inertia can be added to the condition of dropping VFIB flag proportionally to the duration of the episode. For example, for a VFIB episode lasting 1 minute, 1 minute of inertia can be added before the VFIB flag is set to indicate its offset. The combination of these safety measures can provide additional assurance that the critical event is detected and promptly transmitted to the monitoring center.

The systems and techniques described and illustrated in this specification can be implemented in analog electronic circuitry, digital electronic circuitry, integrated circuitry, computer hardware, firmware, software, or in combinations of the forgoing, such as the structural means disclosed in this specification and structural equivalents thereof (e.g., an embedded implementation). Apparatus can be implemented in a software product (e.g., a computer program product) tangibly embodied in a machine-readable medium (e.g., a storage device) for execution by a programmable processor, and processing operations can be performed by a programmable processor executing a program of instructions to perform functions by operating on input data and generating output. Further, the system can be implemented advantageously in one or more software programs that are executable on a programmable system. This programmable system can include the following: 1) at least one programmable processor coupled to receive data and instructions from, and to transmit data and instructions to, a data storage system; 2) at least one input device; and 3) at least one output device. Moreover, each software program can be implemented in a high-level procedural or object-oriented programming language, or in assembly or machine language if desired; and in any case, the language can be a compiled or an interpreted language.

Also, suitable processors include, by way of example, both general and special purpose microprocessors. Generally, a processor will receive instructions and data from a read-only memory, a random access memory, and/or a machine-readable signal (e.g., a digital signal received through a network connection). Generally, a computer will include one or more mass storage devices for storing data files. Such devices can include magnetic disks, such as internal hard disks and removable disks, magneto-optical disks, and optical disks. Storage devices suitable for tangibly embodying software program instructions and data include all forms of non-volatile memory, including, by way of example, the following: 1) semiconductor memory devices, such as EPROM (electrically programmable read-only memory); EEPROM (electrically erasable programmable read-only memory) and flash memory devices; 2) magnetic disks such as internal hard disks and removable disks; 3) magneto-optical disks; and 4) optical disks, such as CD-ROM disks. Any of the foregoing can be supplemented by, or incorporated in, ASICs (application-specific integrated circuits).

To provide for interaction with a user (such as the system operator), the system can be implemented on a computer system having a display device such as a monitor or LCD (liquid crystal display) screen for displaying information to the user and a keyboard and a pointing device such as a mouse or a trackball by which the user can provide input to the computer system. The computer system can be programmed to provide a graphical user interface through which computer programs interact with users and operational settings can be changed in the monitoring system.

The foregoing description has been presented in terms of particular implementations. Other embodiments are within the scope of the following claims. For example, the operations can be performed in a different order and still achieve desirable results; the order of operations illustrated should not be considered limiting. Moreover, alternative implementations can use multiple physiological signals, and dynamical quantities can be based on multiple different types of physiological signals.

What is claimed is:

1. A machine-implemented method comprising:
    obtaining a sensed cardiac signal of an organism, the sensed cardiac signal comprising a time series $x(t)$;
    applying a Hilbert (H) transform to the time series $x(t)$ to obtain $H(x(t))$, wherein $x(t)$ and $H(x(t))$ together forming a partial state space trajectory;
    determining a speed of trajectory, for the sensed cardiac signal, from the partial state space trajectory; and
    identifying physiological information concerning the organism based on a combination of first and second signal elements, the first signal element comprising a phase property or an amplitude property of the speed of trajectory, and the second signal element comprising an amplitude property of the partial state space trajectory;
    wherein the determining and the identifying are performed by one or more data processing apparatus.

2. The method of claim 1, further comprising separating a phase component of the speed of trajectory into a slow component and a fast component, wherein the first signal element comprises the phase property, the phase property being the slow component of the phase component.

3. The method of claim 2, wherein the determining comprises estimating the speed of trajectory in discrete time in a digital processor using finite differences in the partial state space trajectory, and the identifying comprises identifying the physiological information based on the phase property, the phase property being determined from the amplitude property of the speed of trajectory and a component of the speed of trajectory that corresponds to $H(x(t))$.

4. The method of claim 3, wherein the identifying comprises locating a P-wave center and boundaries based on the phase property and at least two thresholds.

5. The method of claim 3, wherein the identifying comprises locating a T-wave end based on change in the combination relative to a determined T-wave center, the combination being the phase property of the speed of trajectory multiplied by the amplitude property of the partial state space trajectory.

6. A machine-readable medium encoding a computer program product operable to cause data processing apparatus to perform operations comprising:
    obtaining a sensed cardiac signal of an organism, the sensed cardiac signal comprising a time series $x(t)$;
    applying a Hilbert (H) transform to the time series $x(t)$ to obtain $H(x(t))$, wherein $x(t)$ and $H(x(t))$ together forming a partial state space trajectory;
    estimating a speed of trajectory, $v(i)$, for the sensed cardiac signal, in discrete time $t \equiv i$, $i=[0 \ldots n]$, using finite differences in the partial state space trajectory, wherein the estimated speed of trajectory $v(i)$ includes a first component corresponding to $x(t)$ and a second component corresponding to $H(x(t))$;
    determining from $v(i)$, by division, a phase property of the estimated speed of trajectory $v(i)$ in accordance with a trigonometric function of phase; and
    identifying physiological information concerning the organism based on the phase property.

7. The machine-readable medium of claim 6, wherein the identifying comprises detecting wave form boundaries in the sensed cardiac signal.

8. The machine-readable medium of claim 7, wherein the detecting comprises detecting the wave form boundaries based on the phase property combined with an amplitude property of the partial state space trajectory.

9. The machine-readable medium of claim 6, wherein the trigonometric function is sine, and the determining comprises dividing the second component of v(i) by an absolute value of v(i).

10. The machine-readable medium of claim 6, wherein the trigonometric function is cosine, and the determining comprises dividing the first component of v(i) by an absolute value of v(i).

11. The machine-readable medium of claim 6, wherein the identifying comprises locating a P-wave center and boundaries using the phase property, an identified Q-point, and at least two thresholds.

12. The machine-readable medium of claim 9, the operations comprising locating a T-wave center using a momentum of trajectory derived from an amplitude property of the partial state space trajectory and an amplitude property of the speed of trajectory, and wherein the identifying comprises locating a T-wave end based on change in a value relative to the T-wave center, the value being the phase property of the estimated speed of trajectory multiplied by the amplitude property of the partial state space trajectory.

13. The machine-readable medium of claim 6, wherein the obtaining comprises receiving a real-time, electrocardiogram time series recorded previously for a human heart.

14. A machine-implemented method comprising:
obtaining a sensed cardiac signal of an organism, the sensed cardiac signal comprising a time series x(t);
applying a Hilbert (H) transform to the time series x(t) to obtain H(x(t)), wherein x(t) and H(x(t)) together forming a partial state space trajectory;
determining a speed of trajectory, for the sensed cardiac signal, from the partial state space trajectory;
combining an amplitude property of the partial state space trajectory with an amplitude property of the speed of trajectory to derive a momentum of trajectory; and
identifying physiological information concerning the organism based on the momentum of trajectory derived from the amplitude property of the partial state space trajectory and the amplitude property of the speed of trajectory;
wherein the determining, the combining, and the identifying are performed by one or more data processing apparatus.

15. The method of claim 14, wherein the identifying the physiological information comprises locating a T-wave center in the sensed cardiac signal based on the momentum of trajectory derived from the amplitude property of the partial state space trajectory and the amplitude property of the speed of trajectory.

16. The method of claim 14, wherein the identifying the physiological information comprises estimating boundaries of a QRS complex in the sensed cardiac signal based on the momentum of trajectory derived from the amplitude property of the partial state space trajectory and the amplitude property of the speed of trajectory.

17. The method of claim 16, wherein estimating the boundaries of the QRS complex comprises locating a Q-point to the left of a maximum in the momentum of trajectory, and locating an S-point to the right of the maximum, based on a predefined portion of the maximum.

18. The method of claim 17, further comprising identifying an R-point based on the maximum in the momentum of trajectory.

19. The method of claim 14, wherein the identifying the physiological information comprises detecting ventricular fibrillation based on the momentum of trajectory derived from the amplitude property of the partial state space trajectory and the amplitude property of the speed of trajectory.

20. The method of claim 19, wherein detecting ventricular fibrillation comprises monitoring periodicity in oscillations of the momentum of trajectory.

21. The method of claim 19, wherein detecting ventricular fibrillation comprises:
maintaining a moving average of the momentum of trajectory; and
monitoring changes in the momentum of trajectory relative to the moving average.

22. A cardiac monitoring apparatus comprising:
an input element;
a processor; and
a machine-readable medium encoding instructions operable to cause the processor to perform operations comprising:
obtaining, from the input element, a sensed cardiac signal of an organism;
applying a Hilbert transform to the sensed cardiac signal to form a partial state space trajectory;
determining a speed of trajectory, for the sensed cardiac signal, from the partial state space trajectory;
combining an amplitude property of the partial state space trajectory with an amplitude property of the speed of trajectory to form a calculated signal; and
identifying physiological information concerning the organism based on the calculated signal.

23. The apparatus of claim 22, wherein the combining comprises forming a calculated signal comprising a momentum of trajectory.

24. The apparatus of claim 23, wherein the identifying comprises detecting ventricular fibrillation based on the momentum of trajectory.

25. The apparatus of claim 23, wherein the identifying comprises locating Q and S points in a QRS complex of the sensed cardiac signal based on the momentum of trajectory.

26. The apparatus of claim 23, wherein the identifying comprises locating a T-wave center in the sensed cardiac signal based on the momentum of trajectory.

27. The apparatus of claim 23, wherein the calculated signal comprises a first calculated signal, the combining comprises forming a second calculated signal from a phase property of the speed of trajectory and the amplitude property of the partial state space trajectory, and the identifying comprises identifying the physiological information concerning the organism based on the first calculated signal and the second calculated signal.

28. The apparatus of claim 27, wherein the identifying comprises locating a T-wave end based on change in the second calculated signal relative to a T-wave center.

29. The apparatus of claim 27, wherein the operations comprise forming a third calculated signal from a phase property of the speed of trajectory; and the identifying comprises identifying the physiological information concerning the organism based on the first calculated signal, the second calculated signal, and the third calculated signal.

30. The apparatus of claim 29, wherein the determining comprises estimating a speed of trajectory, v(i), for the sensed cardiac signal, in discrete time t=i, i=[0 . . . n], using finite differences in the partial state space trajectory, z(i); the first calculated signal is calculated in accordance with $|z(i)\|v(i)|$; the second calculated signal is calculated in accordance with $|z(i)|*Im(v(i))/|v(i)|$; and the third calculated signal is calculated in accordance with $Im(v(i))/|v(i)|$ or $Re(v(i))/|v(i)|$.

31. The apparatus of claim 27, wherein the identifying comprises determining physiological quantities between identified boundaries and centers of wave modes including P-wave, QRS complex, and T-wave.

32. The apparatus of claim 31, wherein the determining comprises finding a first time difference between P-wave onset and Q-point (PR-interval), finding a second time difference between Q-point and S-point (QRS width), finding a third time difference between S-point and T-wave onset (ST segment), finding a fourth time difference between Q-point and T-wave offset (QT interval), finding a fifth time difference between S-point and a T-wave center (T-wave descend), finding a level of the sensed cardiac signal on the ST-segment, and finding a slope of the ST-segment in the sensed cardiac signal.

* * * * *